(12) United States Patent
Grant et al.

(10) Patent No.: US 11,160,677 B2
(45) Date of Patent: Nov. 2, 2021

(54) APPARATUS AND METHOD FOR GASTRIC VOLUME REDUCTION UTILIZING AN EXPANDABLE MEMBER

(71) Applicant: Ethicon, Inc., Somerville, NJ (US)

(72) Inventors: Bethany F. Grant, Scituate, MA (US); Shin-Yir C. Tong, Basking Ridge, NJ (US); John V. Hunt, Cincinnati, OH (US); Jennifer M. Nagy, Flower Mound, TX (US); Elliott J. Fegelman, Cincinnati, OH (US); Kevin S. Weadock, Hillsborough, NJ (US); William E. Cohn, Houston, TX (US); Terry D. Daglow, Houston, TX (US); Nicholas B. Van Stolk, Cincinnati, OH (US); David L. Hamann, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 137 days.

(21) Appl. No.: 16/122,443

(22) Filed: Sep. 5, 2018

(65) Prior Publication Data

US 2020/0069451 A1 Mar. 5, 2020

(51) Int. Cl.
*A61F 5/00* (2006.01)
*A61B 17/00* (2006.01)
(Continued)

(52) U.S. Cl.
CPC ...... *A61F 5/0083* (2013.01); *A61B 17/00234* (2013.01); *A61B 17/3468* (2013.01);
(Continued)

(58) Field of Classification Search
CPC ...... A61F 5/0083; A61F 5/0086; A61F 5/003; A61F 5/0013; A61F 5/0036; A61F 5/0069; A61F 5/0089; A61B 17/1114
See application file for complete search history.

(56) References Cited

U.S. PATENT DOCUMENTS

| 4,133,315 A | 1/1979 | Berman et al. |
| 7,175,589 B2 | 2/2007 | Deem et al. |

(Continued)

FOREIGN PATENT DOCUMENTS

| WO | WO 2005/105003 A1 | 11/2005 |
| WO | WO 2010/087772 A1 | 8/2010 |

OTHER PUBLICATIONS

International Search Report and Written Opinion dated Dec. 19, 2019 for Application No. PCT/IB2019/057243, 13 pgs.
(Continued)

*Primary Examiner* — Katrina M Stransky
*Assistant Examiner* — Mohammed S Adam
(74) *Attorney, Agent, or Firm* — Frost Brown Todd LLC

(57) ABSTRACT

A method is used to reduce a volume of a stomach of a patient. The method includes inverting a portion of a stomach wall to thereby create an inverted portion. An expandable member is positioned adjacent to the outer surface of the inverted portion. The expandable member is expanded to thereby expand the inverted portion. The expanded expandable member has a first outer diameter. A base region of the inverted portion is cinched to thereby capture the expanded expandable member in the expanded inverted portion. The expanded expandable member has a first outer diameter. Expanding and cinching provide a cinch diameter to first outer diameter ratio from approximately 0.5:1 to approximately 0.9:1.

20 Claims, 16 Drawing Sheets

(51) Int. Cl.
*A61B 17/34* (2006.01)
*A61B 17/04* (2006.01)

(52) U.S. Cl.
CPC .. *A61F 5/0076* (2013.01); *A61B 2017/00818* (2013.01); *A61B 2017/0404* (2013.01); *A61B 2017/0454* (2013.01); *A61F 5/003* (2013.01); *A61F 5/005* (2013.01)

(56) References Cited

U.S. PATENT DOCUMENTS

| | | | |
|---|---|---|---|
| 7,214,233 B2 | 5/2007 | Gannoe et al. | |
| 7,695,427 B2 | 4/2010 | Kugler et al. | |
| 7,749,235 B2 | 7/2010 | Sheets, Jr. et al. | |
| 7,892,250 B2 | 2/2011 | Ortiz et al. | |
| 7,914,511 B2 | 3/2011 | Ortiz et al. | |
| 8,070,670 B2 | 12/2011 | Deem et al. | |
| 8,162,969 B2 | 4/2012 | Brister et al. | |
| 8,628,553 B2 | 1/2014 | Voegele et al. | |
| 8,734,475 B2 | 5/2014 | Ekvall et al. | |
| 8,870,907 B2 | 10/2014 | Gaur et al. | |
| 2005/0096673 A1* | 5/2005 | Stack | A61F 5/0076 606/151 |
| 2008/0319435 A1* | 12/2008 | Rioux | A61F 5/005 606/33 |
| 2009/0062824 A1* | 3/2009 | Berg | A61F 5/005 606/157 |
| 2011/0087282 A1 | 4/2011 | Fischvogt | |
| 2011/0295056 A1 | 12/2011 | Aldridge et al. | |
| 2015/0272763 A1* | 10/2015 | Balbierz | A61F 5/0036 600/37 |

OTHER PUBLICATIONS

U.S. Appl. No. 15/664,665, entitled "Method for Assisting a Sphincter," filed Jul. 31, 2017.

* cited by examiner

APPARATUS AND METHOD FOR GASTRIC VOLUME REDUCTION UTILIZING AN EXPANDABLE MEMBER

BACKGROUND

In some patients, including those who are morbidly obese, it may be desirable to provide surgical solutions to reduce the patient's weight. Some surgical procedures for weight loss include a gastric bypass procedure (e.g., a roux-en-Y procedure) and a sleeve gastrectomy.

It may be preferable to provide alternative surgical procedures that are minimally invasive or otherwise require less anatomical remodeling than a gastric bypass procedure or sleeve gastrectomy. This may include procedures that introduce an implant or other substance into or onto the stomach using an endoscope, or otherwise manipulate the wall of the stomach, to effectively reduce the volume of the stomach. Reducing the volume of the stomach may provide weight loss through various mechanisms, including a more rapid gastric emptying rate; metabolic benefits; and/or other results.

Examples of such bariatric surgical procedures are described in U.S. Pat. No. 4,133,315, entitled "Method and Apparatus for Reducing Obesity," issued Jan. 9, 1979, the disclosure of which is incorporated by reference herein; U.S. Pat. No. 8,628,553, entitled "Expanding Adhesive Foam Structure to Reduce Stomach Volume," issued Jan. 14, 2014, the disclosure of which is incorporated by reference herein; U.S. Pat. No. 7,749,235, entitled "Stomach Invagination Method and Apparatus," issued Jul. 6, 2010, the disclosure of which is incorporated by reference herein; U.S. Pat. No. 7,914,511, entitled "Use of Biosurgical Adhesive as Bulking Agent," issued Mar. 29, 2011, the disclosure of which is incorporated by reference herein; U.S. Pat. No. 7,892,250, entitled "Use of Biosurgical Adhesive on Inflatable Device for Gastric Restriction," issued Feb. 22, 2011, the disclosure of which is incorporated by reference herein; U.S. Pub. No. 2011/0295056, entitled "Systems and Methods for Gastric Volume Regulation," published Dec. 1, 2011, now abandoned, the disclosure of which is incorporated by reference herein; U.S. Pat. No. 8,870,907, entitled "Methods and Devices for Deploying and Releasing a Temporary Implant within the Body," issued Oct. 28, 2014, the disclosure of which is incorporated by reference herein; U.S. Pat. No. 8,162,969, entitled "Intragrastic Device," issued Apr. 24, 2012, the disclosure of which is incorporated by reference herein; and International Pat. Pub. No. WO/2010/087772, entitled "An Apparatus for Treating GERD," published Aug. 5, 2010, the disclosure of which is incorporated by reference herein.

While various kinds of devices and techniques have been made and used to effectively reduce the volume of a patient's stomach, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
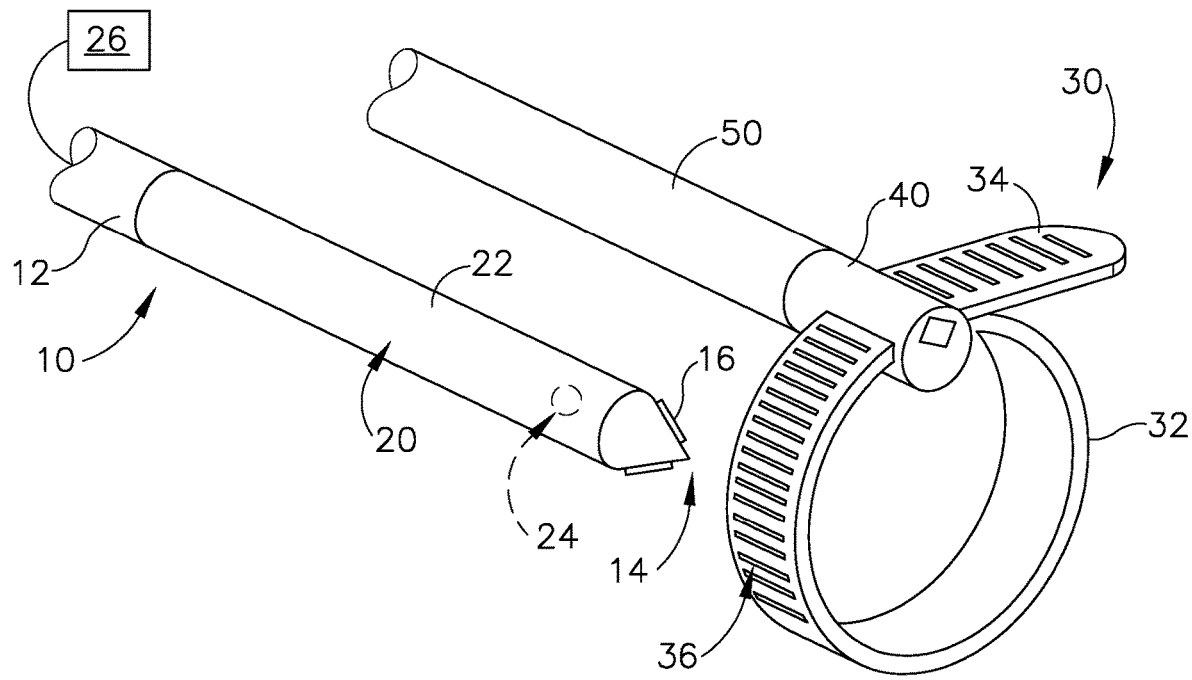
FIG. 1 depicts a perspective view of an exemplary balloon deployment instrument and an exemplary cinch assembly.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", "lower", "top", and "bottom" are defined herein relative to an operator or other operator grasping a surgical instrument having a distal surgical end effector. The term "proximal" refers to the position of an element closer to the operator or other operator, and the term "distal" refers to the position of an element closer to the surgical end effector of the surgical instrument and further away from the operator or other operator. The terms "top" and "upper" refer to the position of the element closer to a top of the surgical instrument when viewed by the operator from above, and the terms "bottom" and "lower" refers to the position of the element closer to a bottom of the surgical instrument when viewed by the operator from below. As such, proximal and distal portions are generally in longitudinal opposition as described herein, whereas upper and lower portions are generally in transverse opposition as described herein. The term "lateral" is also used herein to describe the lateral direction, which is perpendicular to the transverse direction. Such terms are used below with reference to views as illustrated for clarity and are not intended to limit the invention described herein.

I. Exemplary Balloon Deployment Instrument and Cinch Assembly

As noted above, some forms of bariatric surgery (e.g., gastric bypass and sleeve gastrectomy) may remove or reroute more tissue than other procedures. Moreover, such procedures may not otherwise be acceptable for some patients, for various reasons. It may therefore be desirable to provide bariatric surgical procedures that are more patient acceptable yet still effective at providing weight loss. As noted above, procedures that effectively reduce the volume of the stomach may provide an accelerated gastric emptying rate, which may in turn result in weight loss. Examples of such procedures and associated instruments are described in greater detail below. The procedures and associated instruments described below may provide other results, in addition to or in lieu of providing an accelerated gastric emptying rate. An accelerated gastric emptying rate should therefore not be viewed as being a necessary or exclusive result of use of the procedures and instruments described below. By way of example only, use of the procedures and instruments described below may provide metabolic benefits or other results.

A. Overview

Figure 2:
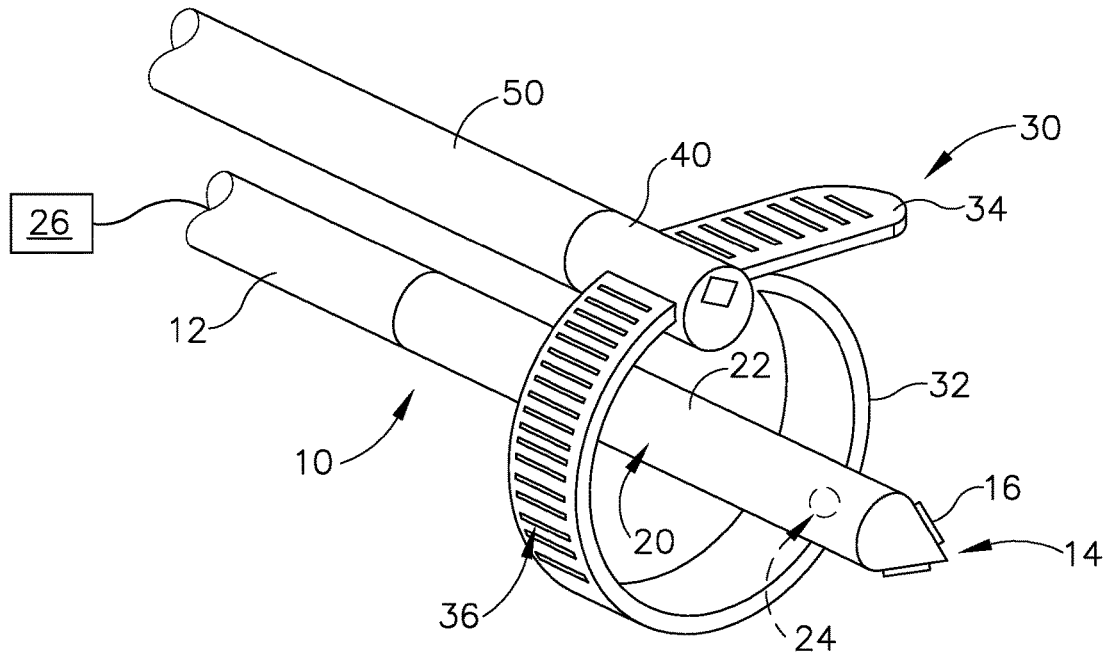
FIG. 2 depicts a perspective view of the balloon deployment instrument and cinch assembly of FIG. 1, with the balloon deployment instrument positioned within a loop formed by the cinch assembly.

FIGS. 1-2 show an exemplary balloon deployment instrument (10) and an exemplary cinch assembly (30) that may be used in a gastric volume reduction procedure as described in greater detail below. Balloon deployment instrument (10) of this example includes a proximal shaft portion (12), a distal shaft portion (20), an inflatable balloon (22) positioned on distal shaft portion (20), and a piercing tip (14). Proximal shaft portion (12) is removably coupled with distal shaft portion (20) in this example, though the two portions (12, 20) may alternatively be coupled together permanently in some other versions.

Balloon deployment instrument (10) is in fluid communication with an inflation fluid source (26). Balloon (22) is configured to receive inflation fluid from inflation fluid source (26) via one or more lateral openings (24) that are formed in distal shaft portion (20) interior to balloon (22). Various suitable ways in which balloon (22) may receive inflation fluid from inflation fluid source (26) will be apparent to those skilled in the art in view of the teachings herein. The inflation fluid may comprise saline, air, or any other suitable fluid as will be apparent to those skilled in the art in view of the teachings herein. Piercing tip (14) of the present example is pointed and has a pair of blades (16), such that piercing tip (14) is configured to pierce a fundus wall (FW) of a stomach (S) as will be described in greater detail below. Other suitable configurations for piercing tip (14) will be apparent to those skilled in the art in view of the teachings herein. While the examples described herein are provided in the context of a fundus wall (FW), the teachings may be readily applied to any other region of a stomach wall (e.g., along the greater curvature of the stomach). The invention is not limited to procedures performed on the fundus wall (FW). The inventors contemplate that the procedures described herein may be performed on any other region of the stomach wall. The reference to the fundus wall (FW) in the examples described herein should not be viewed as limiting in any way.

Cinch assembly (30) of the present example includes a strap (32) having an array of outwardly presented teeth (36). A head (40) is secured to one end of strap (32), with the other end of strap (32) being a free end (34). Strap (32) passes through head (40) as will be described in greater detail below. A winding instrument (50) is removably secured to head (40) and is operable to actuate a winding assembly in head (40) to selectively change the position of free end (34) relative to head (40), thereby adjusting the effective diameter of the loop formed by strap (32), as will also be described in greater detail below. Strap (32) may be formed of a biocompatible plastic and/or any other suitable material(s) as will be apparent to those skilled in the art in view of the teachings herein.

B. Exemplary Gastric Volume Reduction Procedure from within Stomach

Figure 3A:
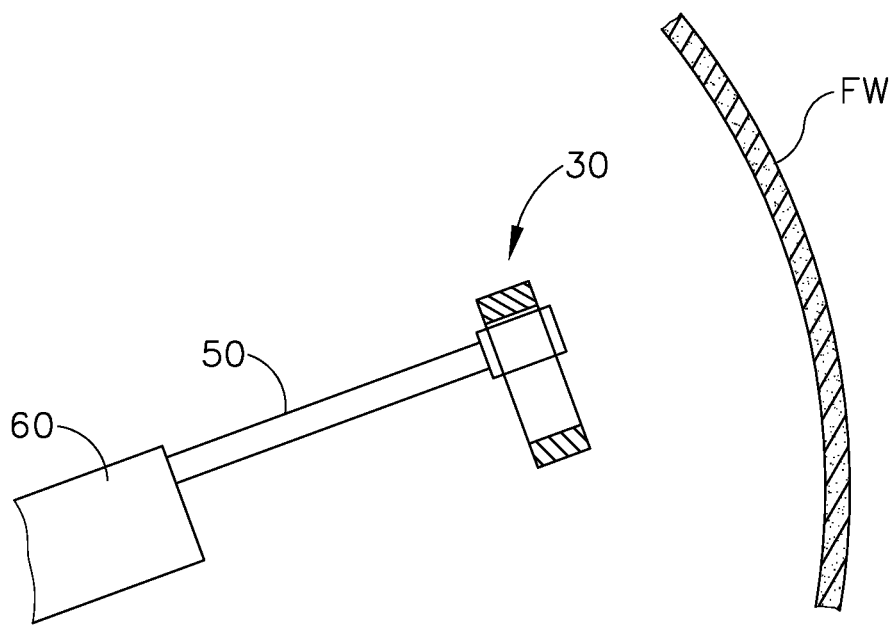
FIG. 3A depicts a schematic cross-sectional view of the cinch assembly of FIG. 1 approaching a fundus wall of a patient's stomach.
Figure 7:
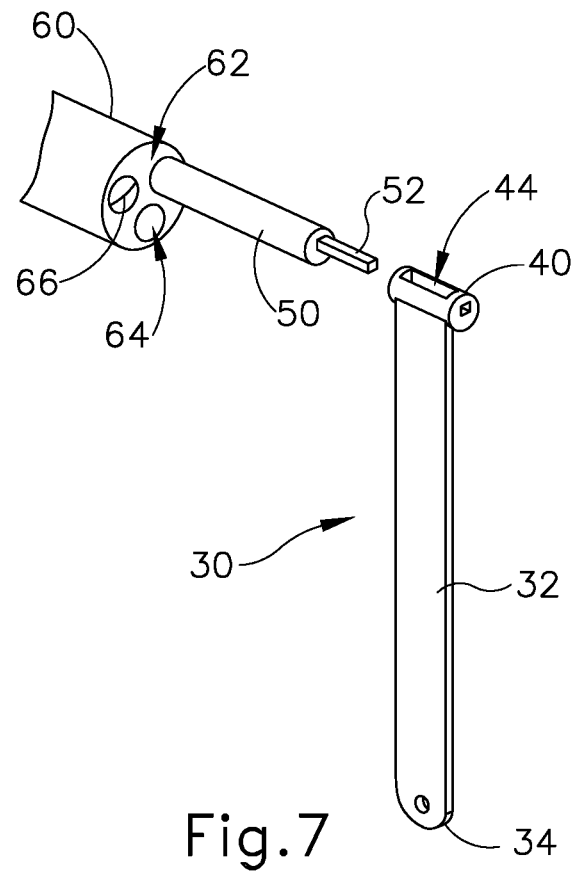
FIG. 7 depicts a perspective view of the winding instrument of FIG. 3H positioned for coupling with the head portion of the cinch assembly of FIG. 1.

FIGS. 3A-3J show an exemplary procedure in which balloon deployment instrument (10) and cinch assembly (30) are used to effectively reduce the volume of a stomach (S) of a patient. As shown in FIG. 3A, winding instrument (50) extends distally from the distal end of a flexible gastroscope (60), which has been inserted into the stomach (S) via the patient's esophagus (E). As shown in FIG. 7, gastroscope (60) of the present example includes two working channels (62, 64) and a camera (66). Winding instrument (50) is slidably disposed in working channel (62) of gastroscope (60). Alternatively, winding instrument (50) may be advanced through an overtube (not shown) about gastroscope (60). Camera (66) may be used to provide visualization to thereby assist in positioning of instrumentation as described below.

Referring back to FIG. 3A, cinch assembly (30) is removably secured to the distal end of winding instrument (50). In some versions, cinch assembly (30) is coupled with winding instrument (50) before the combination of cinch assembly (30) and winding instrument (50) are advanced down the esophagus (E) and into the stomach (S). In some other versions, winding instrument (50) is inserted via gastroscope (60), while cinch assembly (30) is inserted via some other device (e.g., flexile sheath), and then cinch assembly (30) is coupled with winding instrument (50) after cinch assembly (30) and winding instrument (50) are positioned in the stomach (S). Other suitable devices and techniques that may be used to achieve the state shown in FIG. 3A will be apparent to those skilled in the art in view of the teachings herein.

Figure 3B:
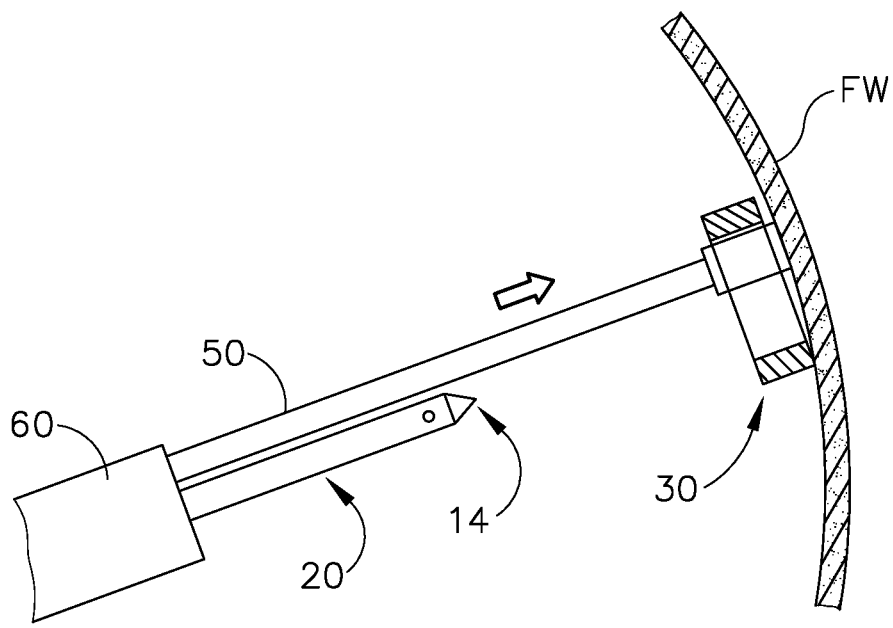
FIG. 3B depicts a schematic cross-sectional view of the cinch assembly of FIG. 1 engaging the fundus wall of FIG. 3A, with the balloon deployment instrument of FIG. 1 being advanced toward the fundus wall.

As also shown in FIG. 3A, cinch assembly (30) is oriented such that the plane defined by the loop of strap (32) is substantially parallel with a region of the fundus wall (FW). As noted above, while the procedures are described herein with reference to the fundus wall (FW), the procedures may also be performed at various other regions of the wall of the stomach (S). The teachings herein are not limited to procedures being performed at the fundus wall (FW). As shown in FIG. 3B, the next stage of the procedure includes advancement of cinch assembly (30) against the fundus wall (FW), such that cinch assembly (30) is engaged with the fundus wall (FW). As also shown in FIG. 3B, balloon deployment instrument (10) is advanced distally from gastroscope (60), with balloon deployment instrument (10) being substantially coaxially aligned with the central axis of the loop formed by strap (32) of cinch assembly (30). Balloon deployment instrument (10) is slidably disposed in working channel (64) of gastroscope (60). Alternatively, balloon deployment instrument (10) may be advanced through an overtube (not shown) about gastroscope (60).

Figure 3C:
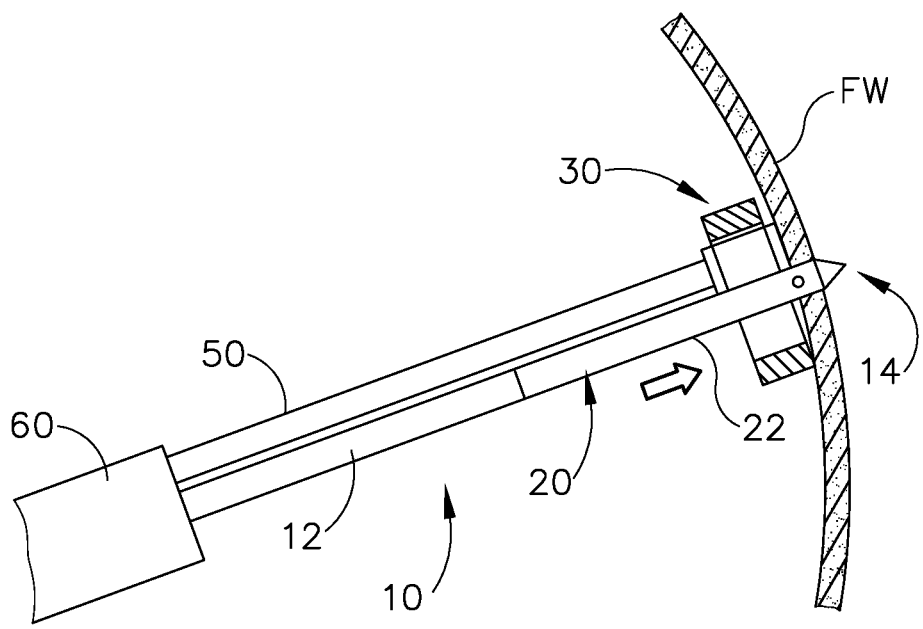
FIG. 3C depicts a schematic cross-sectional view of the cinch assembly of FIG. 1 engaging the fundus wall of FIG. 3A, with the balloon deployment instrument of FIG. 1 piercing the fundus wall.
Figure 3D:
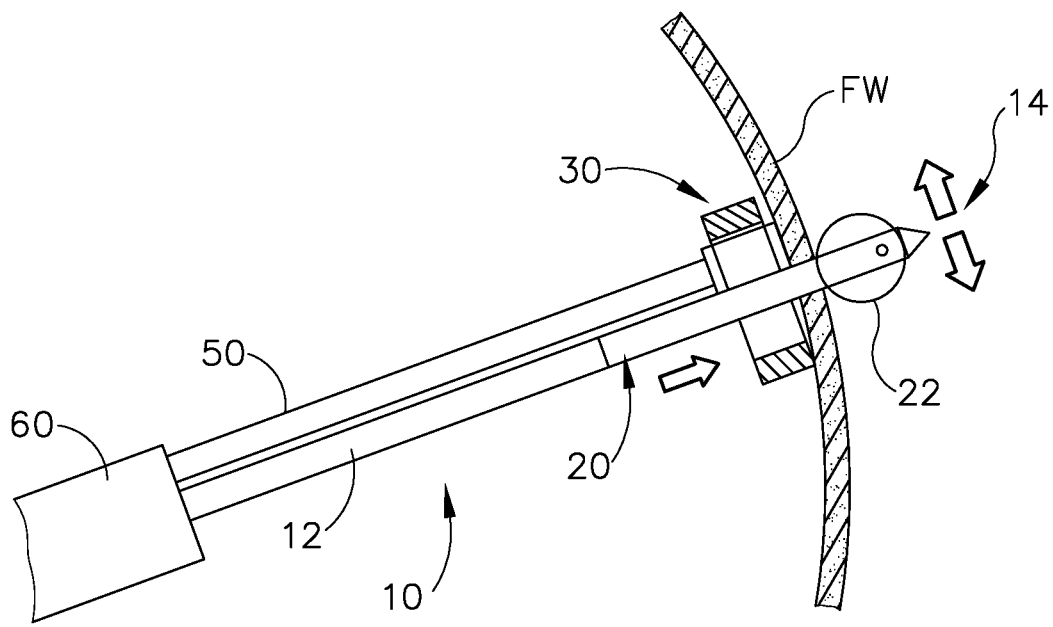
FIG. 3D depicts a schematic cross-sectional view of the cinch assembly of FIG. 1 engaging the fundus wall of FIG. 3A, with a balloon of the balloon deployment instrument of FIG. 1 being inflated on the outside of the fundus wall.

As shown in FIG. 3C, balloon deployment instrument (10) is advanced further such that piercing tip (14) penetrates through the fundus wall (FW). In some other versions, tip (14) is blunt and some other instrument is used to form an opening in the fundus wall (FW) for tip (14) to pass through. As shown in FIG. 3D, balloon deployment instrument (10) is advanced further such that at least a portion of balloon (22) is located outside of the fundus wall (FW), and then balloon (22) is slightly inflated. At this stage, balloon (22) is inflated only to a point where the outer diameter of balloon (22) is less than the inner diameter of the loop formed by band (32) of cinch assembly (30). In some versions, inflation fluid source (26) includes a control feature that automatically halts inflation of balloon (22) when balloon (22) reaches a state of inflation where the outer diameter of balloon (22) is less than the inner diameter of the loop formed by band (32). In addition, inflation fluid source (26) may include a feedback feature that alerts the operator when balloon (22) reaches a state of inflation where the outer diameter of balloon (22) is less than the inner diameter of the loop formed by band (32). Various suitable ways in which such control and feedback may be provided will be apparent to those skilled in the art in view of the teachings herein.

Figure 3E:
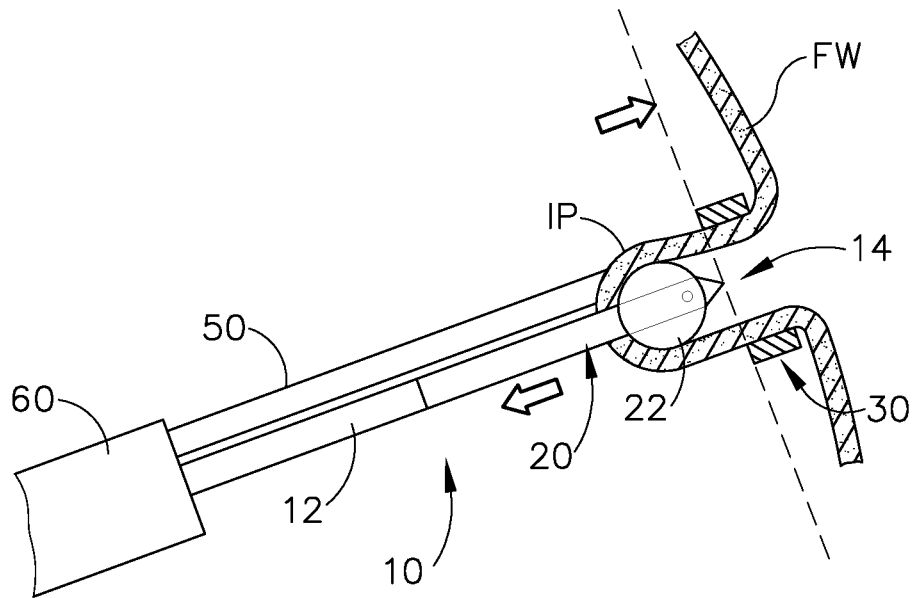
FIG. 3E depicts a schematic cross-sectional view of the cinch assembly of FIG. 1 engaging the fundus wall of FIG. 3A, with the balloon of FIG. 3D pulling a portion of the fundus wall back through a loop of the cinch assembly to thereby form an inverted portion of the fundus wall.

As shown in FIG. 3E, the next stage includes retracting balloon deployment instrument (10) proximally while holding cinch assembly (30) and winding instrument (50) stationary. Balloon (22) is still in the partially deflated state during this retraction. Balloon (22) pulls a portion of the fundus wall (FW) through the loop formed by cinch assembly (30), thereby creating an inverted portion (IP) of the fundus wall (FW) by placating the fundus wall (FW). Balloon deployment instrument (10) is retracted to a point where balloon (22) is proximal to the plane (P) defined by the proximal edge of cinch assembly (30).

Figure 3F:
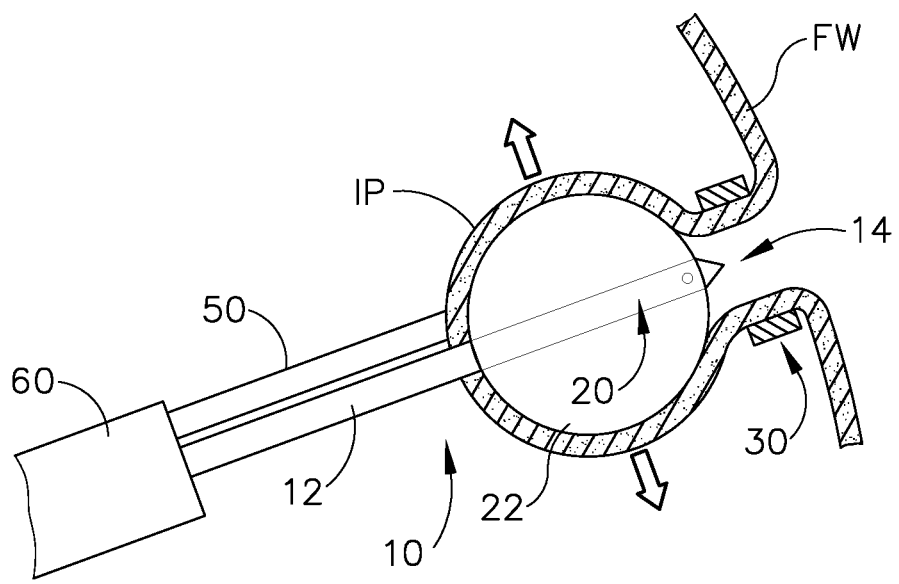
FIG. 3F depicts a schematic cross-sectional view of the cinch assembly of FIG. 1 engaging the fundus wall of FIG. 3A, with the balloon of FIG. 3D being further inflated to enlarge the inverted portion of the fundus wall.

Next, balloon (22) is inflated to expand the inverted portion (IP) of the fundus wall (FW), as shown in FIG. 3F. Balloon (22) is expanded to define an outer diameter that is substantially larger than the inner diameter of the loop defined by strap (32) of cinch assembly (30). In some instances, the outer diameter of balloon (22) at the stage shown in FIG. 3F is predetermined. In some such instances, inflation fluid source (26) is configured to provide a predetermined volume of fluid to balloon (22) to inflate balloon (22) to achieve a prescribed outer diameter. By way of example only, this prescribed outer diameter may be achieved by filling balloon (22) with a precise volume of liquid, by providing measurement feedback of the diameter during filling, or otherwise. For instance, balloon (22) may be filled with a volume of fluid ranging from approximately 200 ml to approximately 300 ml; or in some cases up to approximately 400 ml. By way of further example only, the prescribed outer diameter of inflated balloon (22) may be any diameter from approximately 7 cm to approximately 14 cm; or more particularly from approximately 7 cm to approximately 11.5 cm; or more particularly approximately 8 cm to approximately 10 cm; or more particularly approximately 9 cm.

Figure 3G:
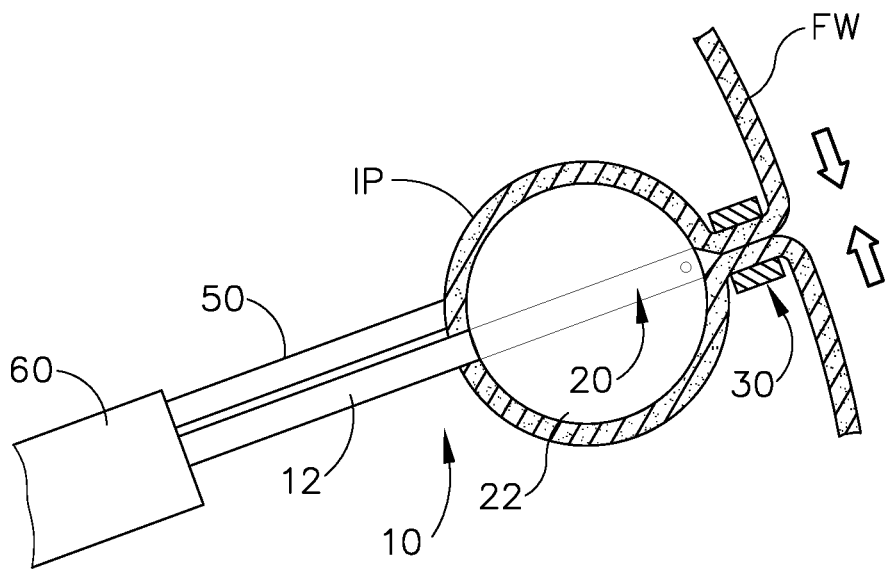
FIG. 3G depicts a schematic cross-sectional view of the cinch assembly of FIG. 1 engaging the fundus wall of FIG. 3A, with the cinch assembly being cinched to effectively close off the enlarged inverted portion of the fundus wall.

With the inverted portion (IP) of the fundus wall (FW) in the expanded state, and with balloon (22) still inflated to the state causing expansion of inverted portion (IP), winding instrument (50) is actuated to cinch up cinch assembly (30) at the base of the inverted portion (IP). This effectively encloses the inflated balloon (22) in the inverted portion (IP), as shown in FIG. 3G. In some instances, the inner diameter formed by cinch assembly (30) at the stage shown in FIG. 3G is predetermined. In some such instances, winding instrument (50) is configured to actuate cinch assembly (30) in a predetermined fashion to achieve a prescribed inner diameter of cinch assembly (30). By way of example only, this prescribed inner diameter may be achieved by providing visual, audible, or tangible feedback signaling that the target diameter has been achieved (e.g., instrument readout, camera, audible click, etc.). By way of further example only, the prescribed inner diameter of cinch assembly balloon (30) may be any diameter from approximately 3.5 cm to approximately 12.6 cm: or more particularly from approximately 6.3 cm to approximately 7 cm; or more particularly approximately 6.6 cm.

The predetermined inner diameter of the cinched cinch assembly (30) may be related to the predetermined outer diameter of the inflated balloon (22). By way of example only, the prescribed inner and outer diameters of cinched cinch assembly (30) and inflated balloon (22), respectively, may have a ratio from approximately 0.5:1 to approximately 0.9:1; or more particularly from approximately 0.6:1 to approximately 0.8:1; or more particularly approximately 0.7:1. By providing a ratio within these parameters, cinch assembly (30) and inflated balloon (22) may provide an appropriate balance between achieving effective reduction in gastric volume while minimizing the risk of cinch assembly (30) migrating through the fundus wall (FW). In some scenarios, cinch assembly (30) is cinched to form an inner diameter that avoids sealing adjacent regions of the fundus wall (FW) against each other. In other words, the prescribed inner diameter of cinch assembly (30) may be selected to leave a gap between inflated balloon (22) and the exterior of the stomach (S), such that balloon (22) is not completely sealed off in the inverted portion (IP) by the fundus wall (FW) tissue that is being cinched by cinch assembly (30). Moreover, the predetermined inner diameter of cinched cinch assembly (30) may be selected to allow some sliding movement of the fundus wall (FW) in relation to cinch assembly (30). Allowing such sliding movement may reduce the likelihood of cinch assembly (30) migrating into or through the fundus wall (FW).

Figure 3H:
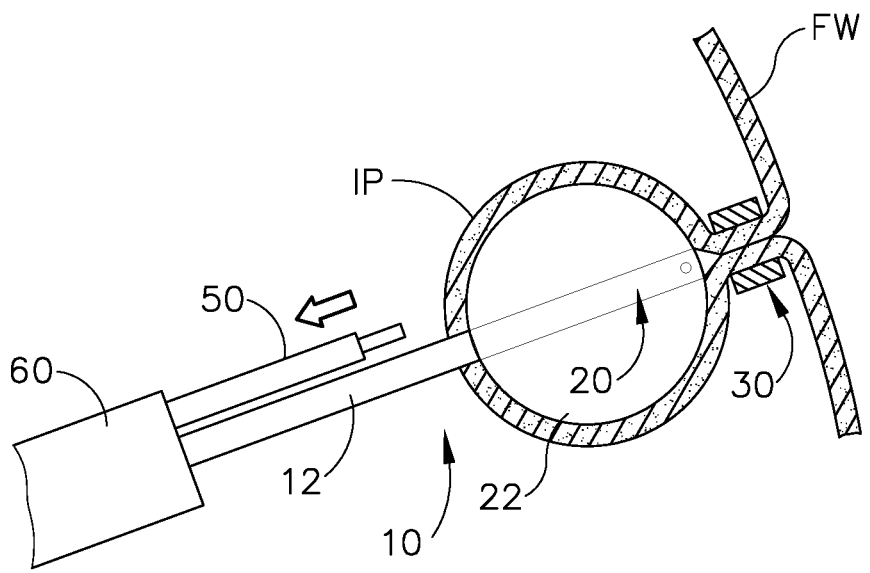
FIG. 3H depicts a schematic cross-sectional view of a winding instrument being retracted to leave the cinch assembly of FIG. 1 cinched at a base of the enlarged inverted portion of the fundus wall.

After cinching cinch assembly (30) to the desired state, winding instrument (50) is then detached from cinch assembly (30) and is withdrawn proximally into gastroscope (60), as shown in FIG. 3H. Cinch assembly (30) remains in the cinched state at the base of the inverted portion (IP).

Figure 3I:
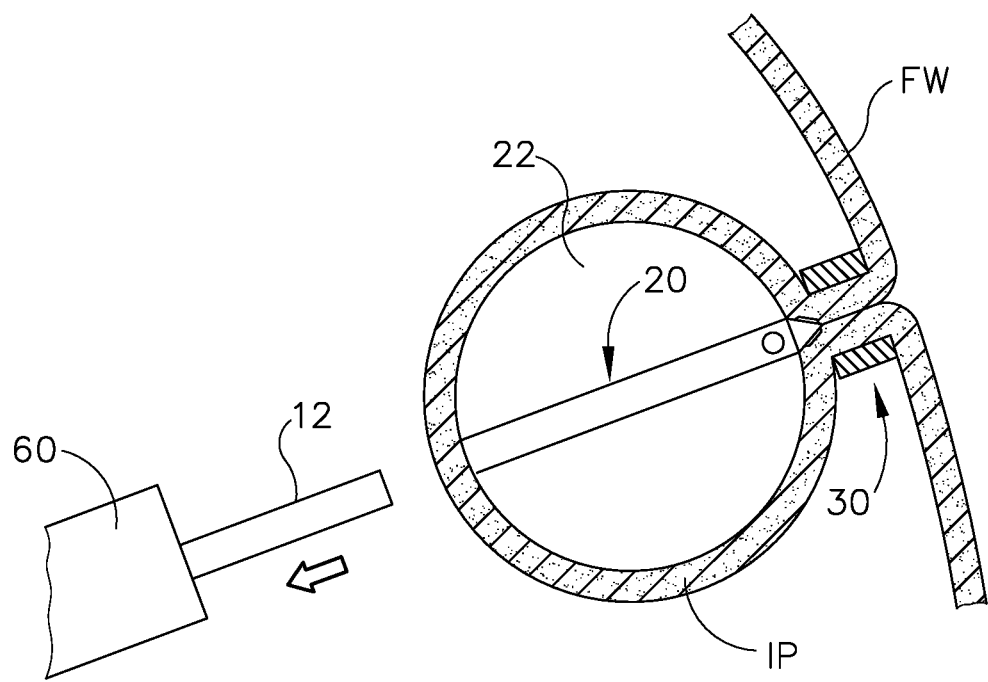
FIG. 3I depicts a schematic cross-sectional view of a shaft portion of the balloon deployment instrument of FIG. 1 being broken away from the balloon and retracted away from the enlarged inverted portion of the fundus wall.

Proximal shaft portion (12) of balloon deployment instrument (10) is then broken away from distal shaft portion (20) of balloon deployment instrument (10), leaving behind distal shaft portion (20) and inflated balloon (22) in the inverted portion (IP) as shown in FIG. 3I. Shaft portions (12, 20) may be removably coupled and decoupled in various ways, including but not limited to latching features, threaded features, frangible features, etc. Various suitable structures and techniques that may be used to removably couple shaft portions (12, 20) together will be apparent to those skilled in the art in view of the teachings herein. In some other versions, balloon (22) is removably coupled with distal shaft portion (20), and shaft portions (12, 20) are retracted together unitarily, leaving behind inflated balloon (22) in the inverted portion (IP). Various suitable ways in which balloon (22) may be removably coupled with distal shaft portion (20) will be apparent to those skilled in the art in view of the teachings herein. In either case, one or both of shaft portions (12, 20) may leave an exit wound in the inverted portion (IP) of the fundus wall (FW). In some versions, the exit wound is small enough to be self-sealing. In some other versions, another instrument is inserted through a working channel of gastroscope (60) to apply a suture, clip, adhesive, or other form of wound closure to the exit wound left by one or both of shaft portions (12, 20) after balloon deployment instrument (10) is retracted into gastroscope (60).

Figure 3J:
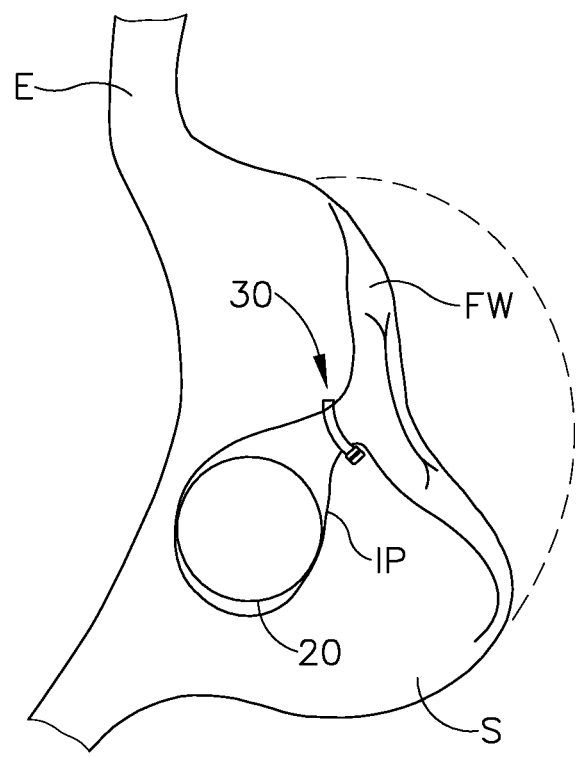
FIG. 3J depicts a schematic view of the stomach of FIG. 3A with the balloon of FIG. 3D secured to the enlarged inverted portion of the fundus wall, with the cinch assembly of FIG. 1 cinched at a base of the enlarged inverted portion of the fundus wall.

After balloon deployment instrument (10) is retracted into gastroscope (60), gastroscope (60) may be extracted from the patient via the esophagus (E). FIG. 3J shows the stomach (S) at the end of the procedure. As shown, the inflated balloon (22) is captured in the inverted portion (IP) of the fundus wall (FW) and is retained therein by cinch assembly (30). The broken lines indicate the previous position of the fundus wall (FW), thereby illustrating the extent to which the volume of the stomach (S) has been effectively reduced. As noted above, this reduction of stomach (S) volume may result in weight loss for the patient through an accelerated gastric emptying rate or other mechanism.

In some scenarios, the inflated balloon (22) and cinch assembly (30) are kept in place as shown in FIG. 3J for a certain period of time; until the patient presents a desired amount of weight loss; or until some other particular condition (or combination of conditions) occurs. Then, balloon (22) is deflated and removed from the inverted portion (IP) of the fundus wall (FW). After balloon (22) is removed, cinch assembly (30) may also be actively removed from the patient. In some instances, cinch assembly (30) may simply fall off of the inverted portion (IP) after balloon (22) is deflated. A grasping instrument may be introduced into the stomach via a gastroscope (60) or via a flexible tube, and the grasping instrument may grasp cinch assembly (30) to remove cinch assembly transesophageally. Alternatively, cinch assembly (30) may simply be passed through the rest of the patient's gastrointestinal tract as part of the normal digestive process.

In some other scenarios, cinch assembly (30) is cinched to a point where the tissue of the fundus wall (FW) effectively seals the inflated balloon (22) within the inverted portion (IP), and the apposed tissue within the loop of cinch assembly (30) eventually necroses. This may lead to the inverted portion (IP) effectively falling away from the rest of the fundus wall (FW), with scar tissue effectively sealing the former base of the inverted portion (IP) in the fundus wall (FW). This may result in a permanent gastric volume reduction. In some such scenarios, the separated inverted portion (IP), including the inflated balloon (22) and cinch assembly (30), may simply be passed through the rest of the patient's gastrointestinal tract as part of the normal digestive process. As another variation of this scenario, balloon (22) and/or cinch assembly (30) may be formed of a bioabsorbable material, with the integrity of balloon (22) and cinch assembly (30) being maintained for at least the duration of the tissue healing and necrosis.

C. Exemplary Cinch Assemblies

Figure 6:
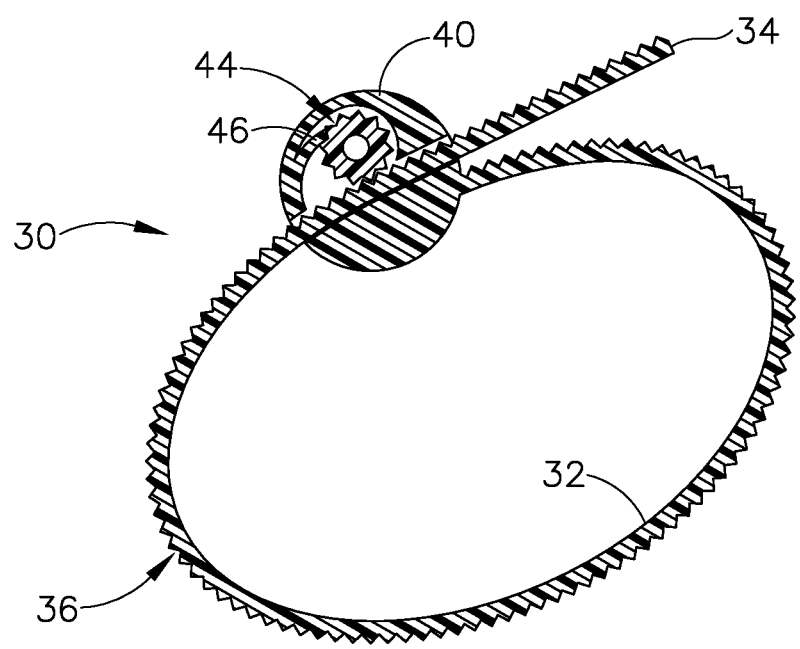
FIG. 6 depicts a cross-sectional view of the cinch assembly of FIG. 1, with a strap of the cinch assembly disposed in a slot of a head portion of the cinch assembly.

FIGS. 4-8C show cinch assembly (30) in greater detail. As shown and as noted above, cinch assembly (30) of the present example includes a strap (32) with teeth (36), a head (40), and a free end (34). Head (40) includes a slot (42) and a female winding key member (44). Slot (42) is configured to receive free end (34) to form a loop with strap (32). As shown in FIG. 6, female winding key member (44) is coupled with a spur gear (46), which is in a meshing relationship with teeth (36) of strap (32) like a rack and pinion mechanism.

Figure 4:
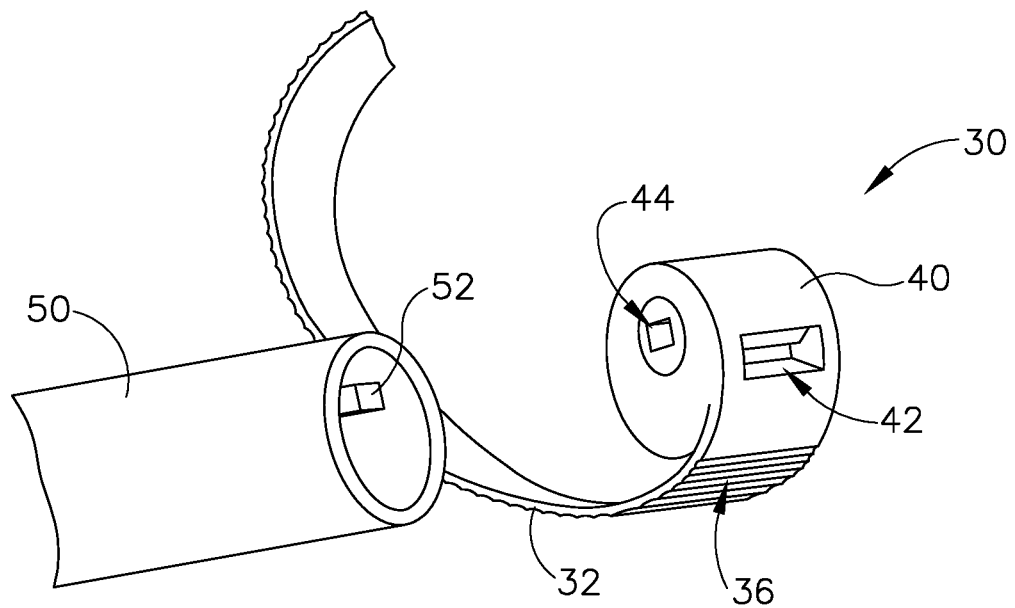
FIG. 4 depicts a perspective view of the cinch assembly of FIG. 1 separated from the winding instrument of FIG. 3H.
Figure 5:
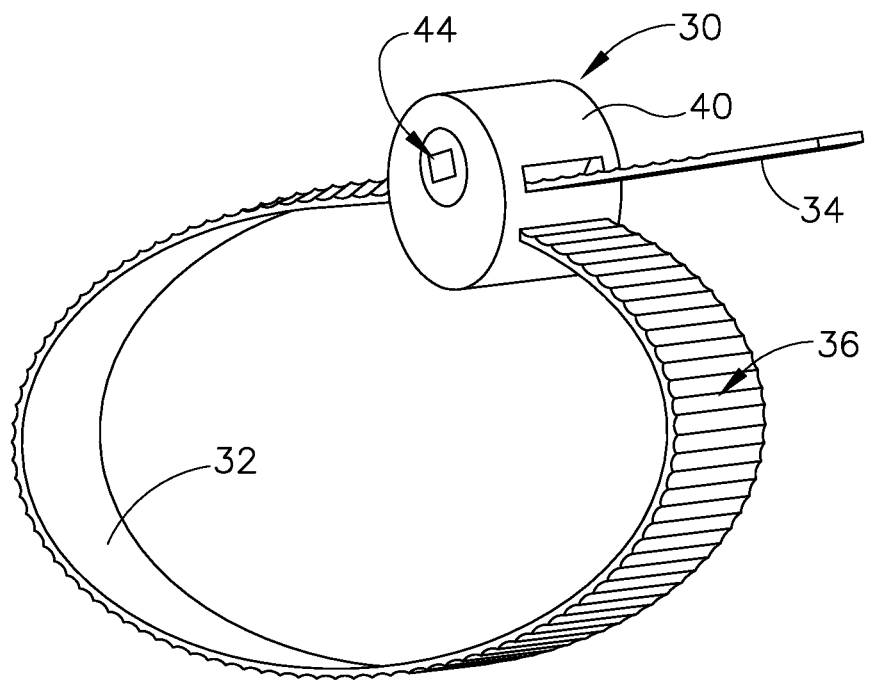
FIG. 5 depicts a perspective view of the cinch assembly of FIG. 1, with a strap of the cinch assembly disposed in a slot of a head portion of the cinch assembly.
Figure 8A:
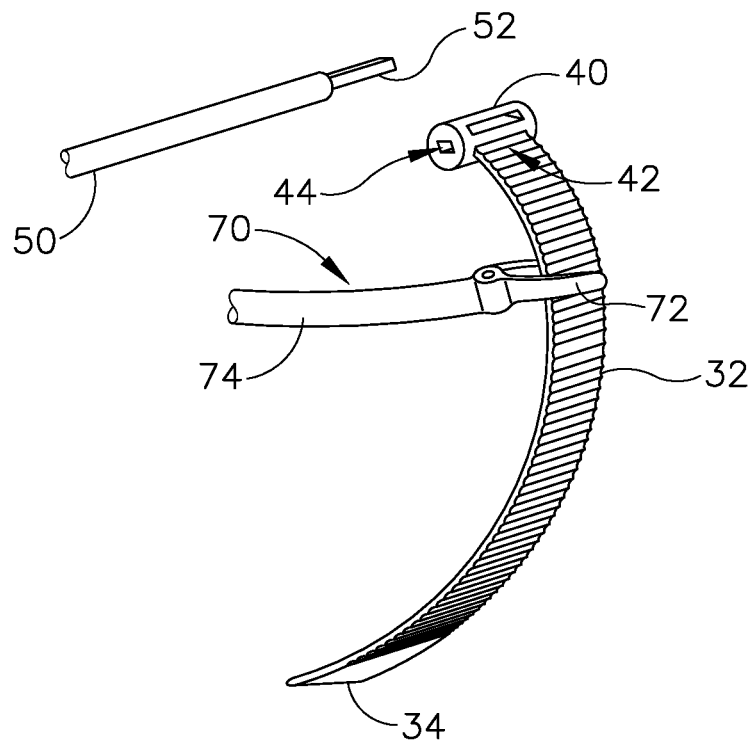
FIG. 8A depicts a perspective view of the cinch assembly of FIG. 1 being grasped by a grasping instrument while the winding instrument of FIG. 3H is being positioned for coupling with the head portion of the cinch assembly.

As shown in FIGS. 4, 7, and 8A, winding instrument (50) includes a male winding key member (52) that is configured to fit in female winding key member (44) of head (40). Winding instrument (50) also includes an actuator (not shown) that is operable to rotate male winding key member (52). When male winding key member (52) is disposed in female winding key member (44), rotary motion of key members (44, 52) will cause rotation of spur gear (46), which will drive translation of free end (34) of strap (32) relative to head (40). The operator may thus actuate winding instrument (50) to selectively adjust the diameter of the loop formed by strap (32). In some versions, head (40) includes a locking feature that selectively maintains the position of free end (34) relative to head (40). For instance, head (40) may include a pawl or other ratcheting feature that is biased to only allow winding instrument (50) to drive spur gear (46) to effectively reduce the diameter of the loop formed by strap (32). Such a pawl or other ratcheting feature may be directly engaged with teeth (36), may be directly engaged with spur gear (46), or may otherwise be engaged. Such a pawl or other ratcheting feature may also include a release that is operable to selectively disengage the pawl or other ratcheting feature, thereby enabling the operator to translate free end (34) relative to head (40) in the opposite direction (e.g., to loosen strap (32) or remove free end (34) from head (40), etc.). Other suitable ways in which cinch assembly (30) may provide movement and selective locking of free end (34) relative to head (40) will be apparent to those skilled in the art in view of the teachings herein.

Figure 8B:
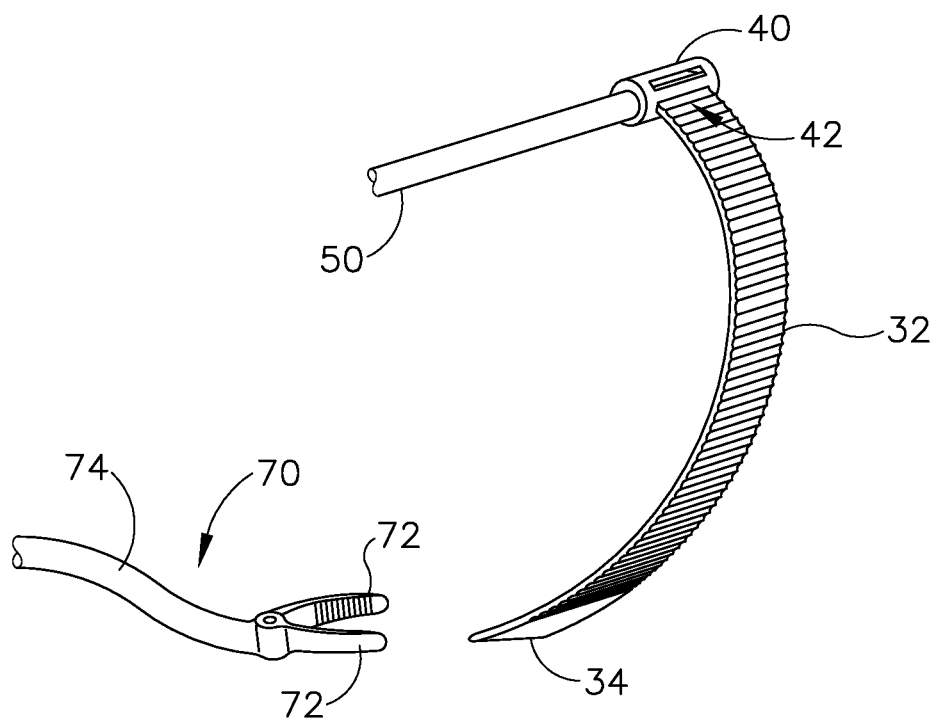
FIG. 8B depicts a perspective view of the winding instrument of FIG. 3H coupled with the head portion of the cinch assembly of FIG. 1, with the grasping instrument of FIG. 8A being repositioned to grasp a free end of a strap of the cinch assembly.
Figure 8C:
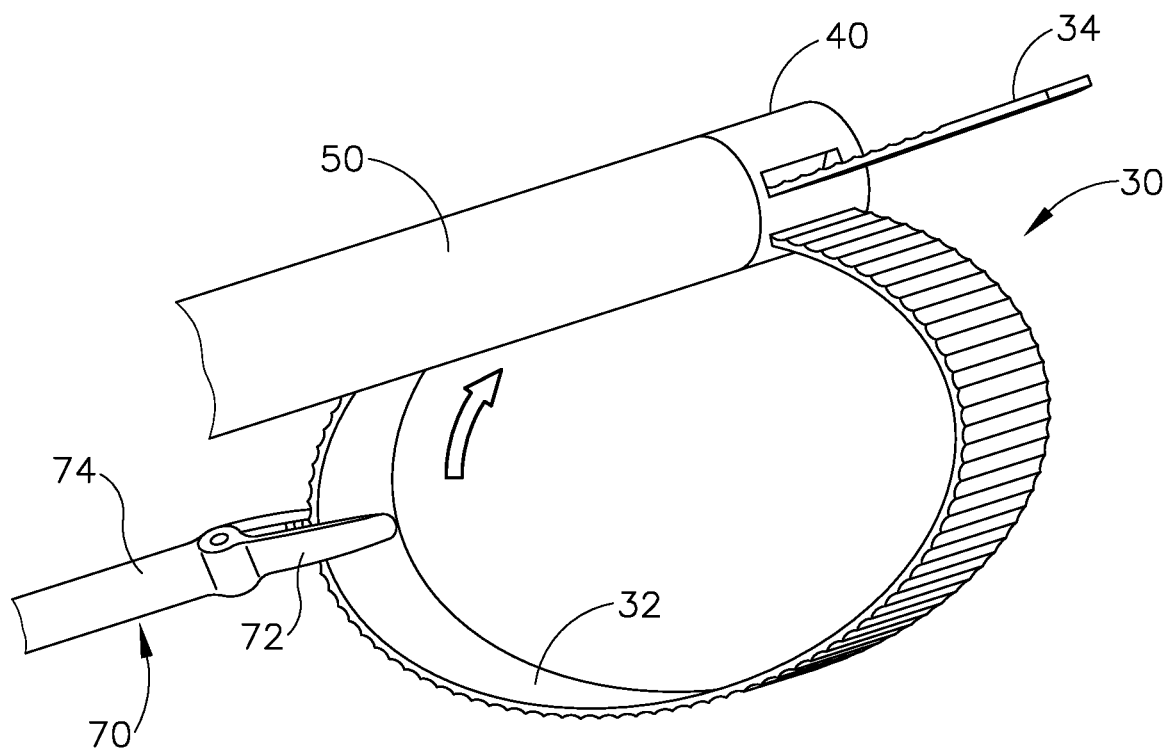
FIG. 8C depicts a perspective view of the winding instrument of FIG. 3H coupled with the head portion of the cinch assembly of FIG. 1, with the grasping instrument of FIG. 8A being used to urge the free end of the strap through the slot in the head portion.

FIGS. 8A-8C show an exemplary method of preparing cinch assembly (30) for the procedure of FIGS. 3A-3J. The procedure of FIGS. 8A-8C may be performed endoscopically within the interior space of the stomach (S). As shown in FIG. 8A, a conventional grasping instrument (70) is used to grasp cinch assembly (30) via strap (32). Grasping instrument (70) includes a shaft (74) and an end effector formed by grasping jaws (72). Grasping instrument (70) may be introduced, with strap (32) being grasped by jaws (72), via a sheath (not shown) that is disposed in the esophagus (E), to thereby reach the interior space of the stomach (S). Alternatively, grasping instrument (70) and cinch assembly (30) may be moved into position in the stomach (S) in any other suitable fashion. Winding instrument (50) may be advanced into the interior space of the stomach (S) via a working channel of a gastroscope (60) or in any other suitable fashion. In the present example, grasping instrument (70) is positioned with jaws (72) near head (40) to stabilize head (40) for insertion of male winding key member (52) into female winding key member (44).

Once cinch assembly (30) and winding instrument (50) are positioned near each other as shown in FIG. 8A, male winding key member (52) may be inserted into female winding key member (44), thereby coupling winding instrument (50) with cinch assembly (30) as shown in FIG. 8B. Grasping instrument (70) releases the portion of strap (32) near head (40) and is moved to position jaws (72) near free end (34) of strap (32), as also shown in FIG. 8B. While winding instrument (50) holds head (40) stationary, grasping instrument (70) is used to feed free end (34) through slot (42), thereby engaging teeth (36) of strap (32) with spur gear (46) of head (40), as shown in FIG. 8C. Grasping instrument (70) may then be removed; and winding instrument (50) and cinch assembly (30) may together be positioned as shown in FIG. 3A to begin the process of FIGS. 3A-3J.

Figure 9:
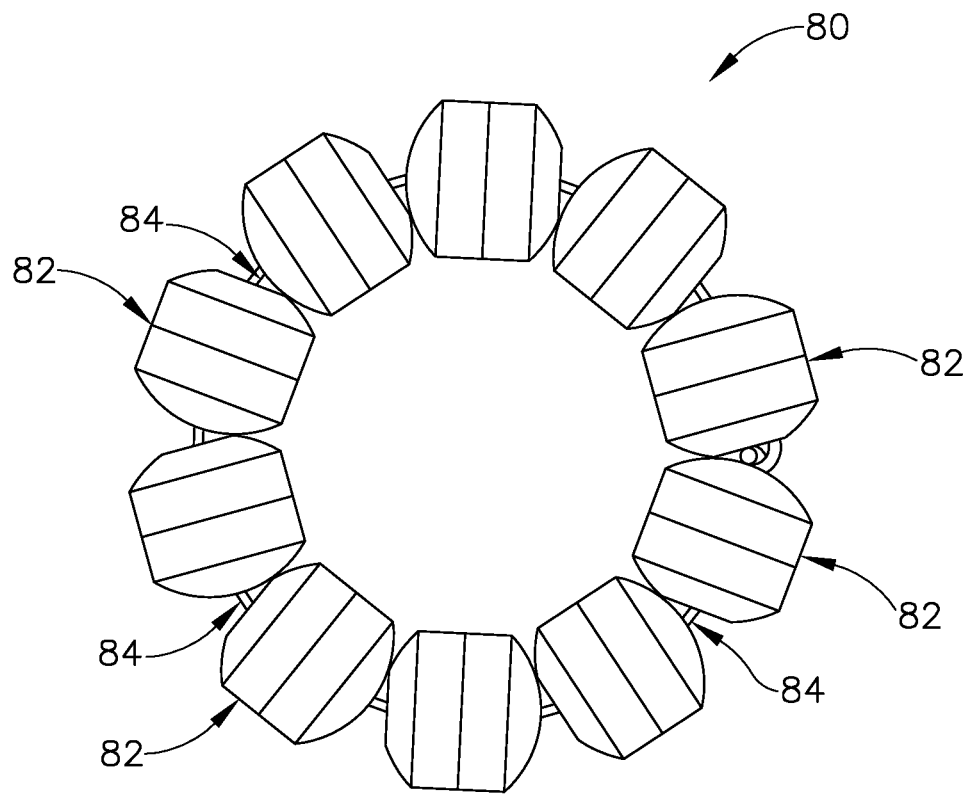
FIG. 9 depicts a top plan view of an exemplary alternative cinch assembly.

FIG. 9 shows an exemplary alternative cinch assembly (80) that may be used as a substitute for cinch assembly (30). Cinch assembly (80) of this example includes a plurality of magnetic beads (82) that are joined together by a plurality of links (84). By way of example only, links (84) may be formed of titanium, nitinol, or any other suitable material(s). While links (84) are configured to maintain beads (82) in an annular arrangement, beads (82) are configured to slide along links (84) to thereby provide a variable effective diameter for cinch assembly (80). Magnetic elements of beads (82) are configured such that each bead (82) is attracted to the adjacent bead (82). This magnetic attraction magnetically biases cinch assembly (80) toward a radially contracted state. In some versions, one of beads (82) is replaced with a latching assembly, which enables cinch assembly (80) to be introduced to the interior region of the stomach (S) in a linear configuration. The latching members of the latching assembly may then be joined together in the stomach (S) to provide cinch assembly (80) in the annular configuration shown in FIG. 9. As another merely illustrative alternative, one link (84) may be broken into two segments that may be joined together via a latch, clasp, suture, or other structure.

By way of further example only, cinch assembly (80) may be constructed and operable in accordance with at least some of the teachings of U.S. Pat. No. 7,175,589, entitled "Methods and Devices for Luminal and Sphincter Augmentation," issued Feb. 13, 2007, the disclosure of which is incorporated by reference herein; U.S. Pat. No. 7,695,427, entitled "Methods and Apparatus for Treating Body Tissue Sphincters and the Like," issued Apr. 13, 2010, the disclosure of which is incorporated by reference herein; U.S. Pat. No. 8,070,670, entitled "Methods and Devices for Luminal and Sphincter Augmentation," issued Dec. 6, 2011, the disclosure of which is incorporated by reference herein; U.S. Pat. No. 8,734,475, entitled "Medical Implant with Floating Magnets," issued May 27, 2014, the disclosure of which is incorporated by reference herein; and/or U.S. patent application Ser. No. 15/664,665, entitled "Method for Assisting a Sphincter," filed Jul. 31, 2017, issued as U.S. Pat. No. 10,405,865 on Sep. 10, 2019, the disclosure of which is incorporated by reference herein. Other suitable ways in which cinch assembly (80) may be configured and operable will be apparent to those skilled in the art in view of the teachings herein.

D. Exemplary Gastric Volume Reduction Procedure Including Percutaneous Approach

In the procedure shown in FIGS. 3A-3J, all the instruments that are used to perform the procedure are introduced into the interior region of the stomach (S) via the esophagus (E). In some scenarios, it may be desirable to introduce one or more instruments percutaneously, via the abdominal wall (AW), to the exterior of the stomach (S). The following describes two exemplary procedures in which at least one instrument is introduced percutaneously, via the abdominal wall (AW), to the exterior of the stomach (S), to provide a reduction in volume of the stomach (S).

Figure 10A:
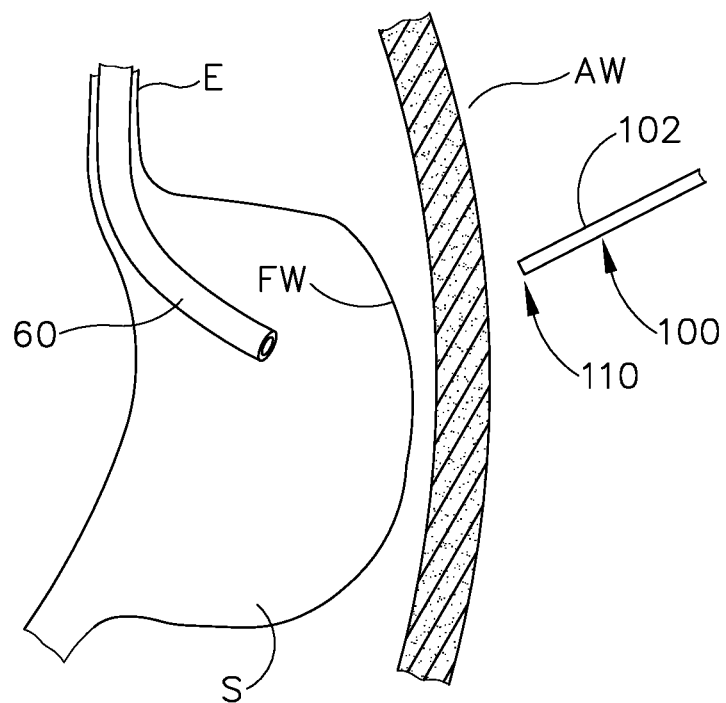
FIG. 10A depicts a schematic cross-sectional view of an exemplary alternative balloon deployment instrument positioned outside an abdominal wall of a patient, with an gastroscope positioned within the stomach of the patient.

FIG. 10A shows the beginning of an exemplary procedure in which a gastroscope (60) is positioned in the interior region of the stomach (S) via the esophagus (E); while a balloon deployment instrument (100) is positioned outside of the patient's abdominal wall (AW). Balloon deployment instrument (100) of this example comprises a shaft (102) with a distal end (110). Distal end (110) is positioned and oriented at a region of the abdominal wall (AW) corresponding to the fundus wall (FW) of the stomach (S). In some versions, light is emitted from gastroscope (60), and such light is discernable through the abdominal wall (AW) to assist the physician in guiding balloon deployment instrument (100) to the appropriate region of the abdominal wall (AW) over the region of the stomach (S) where the distal end of gastroscope (60) is positioned. As noted above, the procedure described below may be performed at other regions of the stomach (S) and is not necessarily limited to the fundus wall (FW). The reference to the fundus wall (FW) in this merely illustrative example should not be viewed as limiting in any way.

Figure 10B:
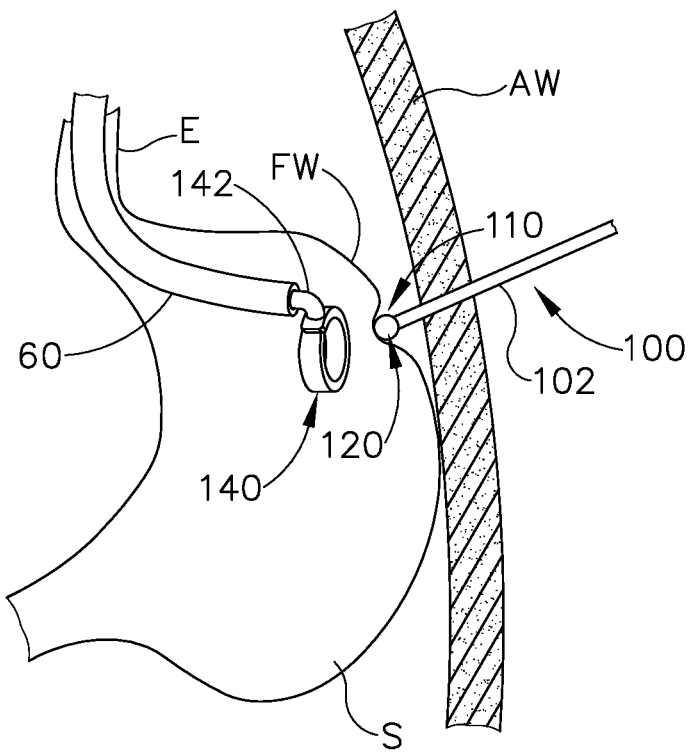
FIG. 10B depicts a schematic cross-sectional view of the balloon deployment instrument of FIG. 10A passed through the abdominal wall of FIG. 10A, with a partially inflated balloon of the balloon deployment instrument being pushed into the fundus wall of the stomach, and with an exemplary cinch assembly being deployed from the gastroscope of FIG. 10A.

Next, as shown in FIG. 10B, balloon deployment instrument (100) is advanced through the abdominal wall (AW), and a balloon (120) at distal end (110) is slightly inflated against the fundus wall (FW). In some versions, distal end (110) is sharp and is thereby configured to pierce the abdominal wall (AW). In some other versions, distal end (110) is blunt and some other instrument is used to pierce the abdominal wall (AW). As yet another merely illustrative example, a conventional trocar may be inserted through the abdominal wall (AW), and balloon deployment instrument (100) may be inserted through the trocar to reach the position shown in FIG. 10B. In any case, light emitted from gastroscope (60) (or from some other source within the stomach (S)) may be used for guidance as to the appropriate location to pierce or otherwise form an incision in the abdominal wall (AW). As is also shown in FIG. 10B, a cinch assembly (140) is positioned near the fundus wall (FW), from the interior region of the stomach (S); and is secured to a deployment shaft (142). Cinch assembly (140) may be configured and operable like cinch assemblies (30, 80) described above; or may have any other suitable configuration and operability.

Figure 10C:
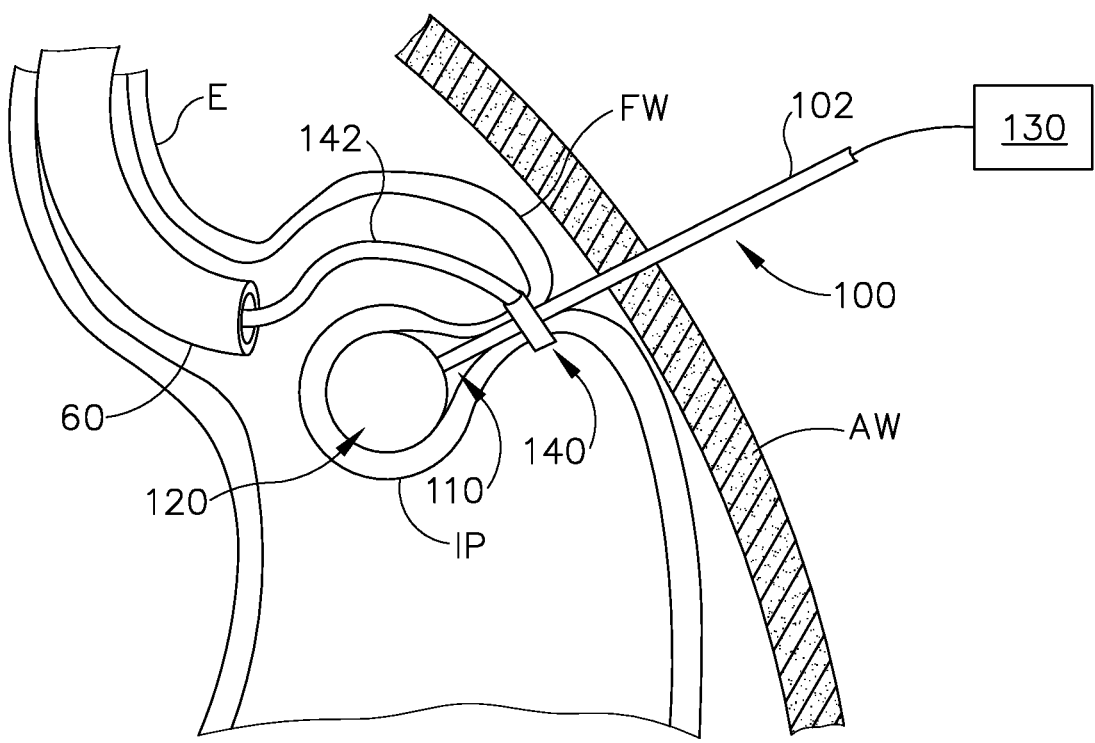
FIG. 10C depicts a schematic cross-sectional view of the balloon deployment instrument of FIG. 10A passed through the abdominal wall of FIG. 10A, with the balloon of FIG. 10B being further inflated to enlarge an inverted portion of the fundus wall, and with the cinch assembly of FIG. 10B being used to cinch the base of the enlarged inverted portion.
Figure 10D:
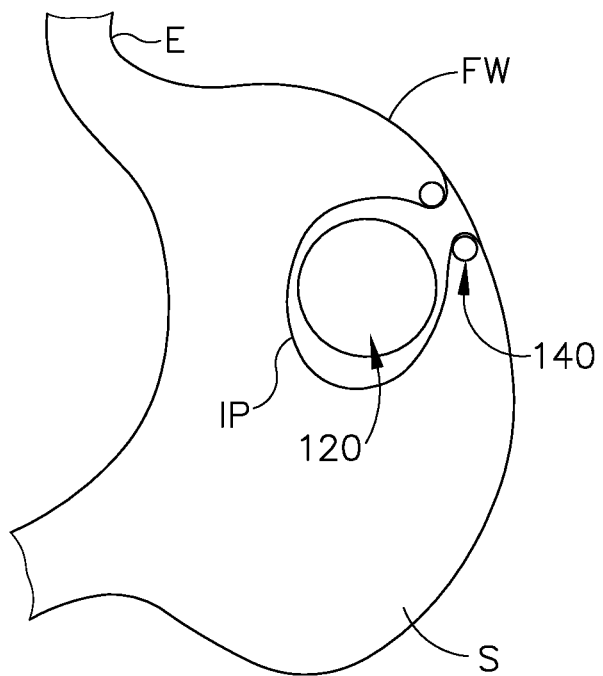
FIG. 10D depicts a schematic view of the stomach of FIG. 10A with the balloon of FIG. 10B secured to the enlarged inverted portion of the fundus wall, with the cinch assembly of FIG. 10B cinched at a base of the enlarged inverted portion of the fundus wall.

As shown in FIG. 10C, balloon deployment instrument (100) is advanced further into the fundus wall (FW), thereby creating an inverted portion (IP), and balloon (120) is further expanded with fluid from a fluid source (130) to thereby expand the inverted portion (IP). As noted above with respect to balloon (22), balloon (120) may be inflated to achieve a predetermined outer diameter; and this may be accomplished through the configuration of fluid source (130). Cinch assembly (140) is placed at the base of the inverted portion (IP) and is then cinched about the base of the inverted portion (IP). As noted above with respect to cinch assembly (30), cinch assembly (140) may be actuated to define a predetermined inner diameter. Shaft (102) is then detached from the inflated balloon (120), leaving the inflated balloon (120) in the inverted portion (IP) as shown in FIG. 10D. The inflated balloon (120) is captured in the inverted portion (IP) of the fundus wall (FW) and is retained therein by cinch assembly (140). The presence of inverted portion (IP) reduces the effective volume of the stomach (S). As noted above, this reduction of stomach (S) volume may provide an accelerated gastric emptying rate, which may in turn result in weight loss for the patient. As also described above, this reduction of stomach (S) volume may be provided on a temporary or permanent basis.

Figure 11A:
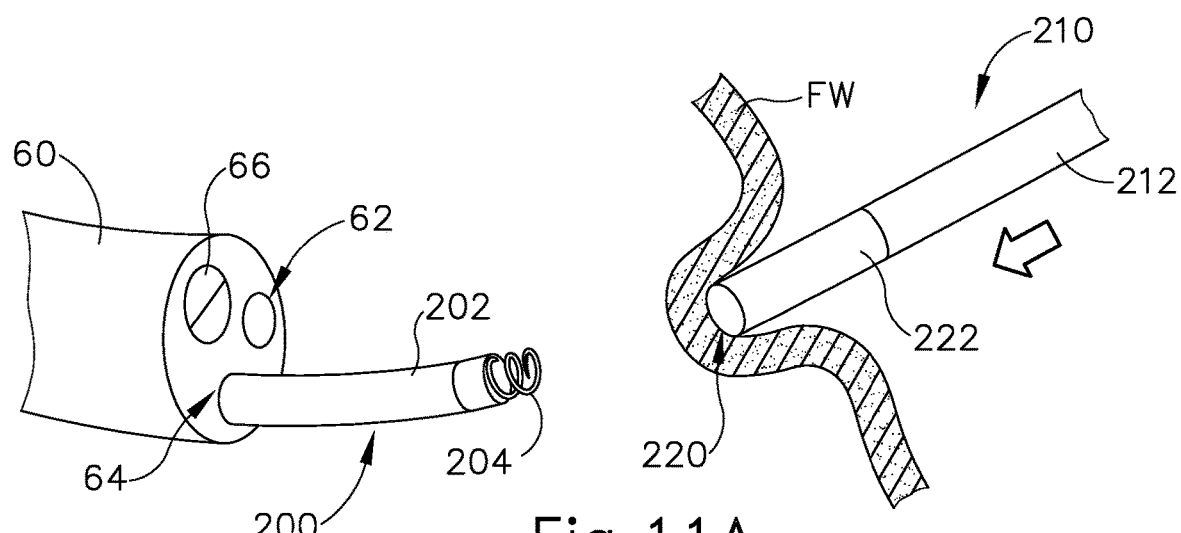
FIG. 11A depicts a schematic view of an exemplary end-grasp instrument approaching an interior side of stomach fundus wall as an exemplary balloon deployment instrument pushes against an exterior side of the fundus wall.

FIGS. 11A-11G show another exemplary gastric volume procedure in which an instrument is introduced percutaneously to engage the exterior of the patient's stomach (S). As shown in FIG. 11A, a balloon deployment instrument (210) is pressed into the fundus wall (FW) from the exterior of the stomach (S). As noted above, the procedure described below may be performed at other regions of the stomach (S) and is not necessarily limited to the fundus wall (FW). The reference to the fundus wall (FW) in this merely illustrative example should not be viewed as limiting in any way. Balloon deployment instrument (210) includes a shaft (212) with a balloon (222) near a blunt distal tip (220). By way of example only, balloon deployment instrument (210) may be advanced to this position via a trocar inserted in the abdominal wall (AW). As is also shown in FIG. 11A, a gastroscope (60) is positioned in the interior of the stomach (S). As described above, gastroscope (60) may be inserted via the esophagus (E). An end-grasp instrument (200) is advanced through a working channel (64) of gastroscope (60). End-grasp instrument (200) includes a shaft (202) and a helical engagement feature (204) at the distal end of shaft (202). While end-grasp instrument (200) of the present example has a helical engagement feature (204), any other suitable tissue engagement structures may be used.

Figure 11B:
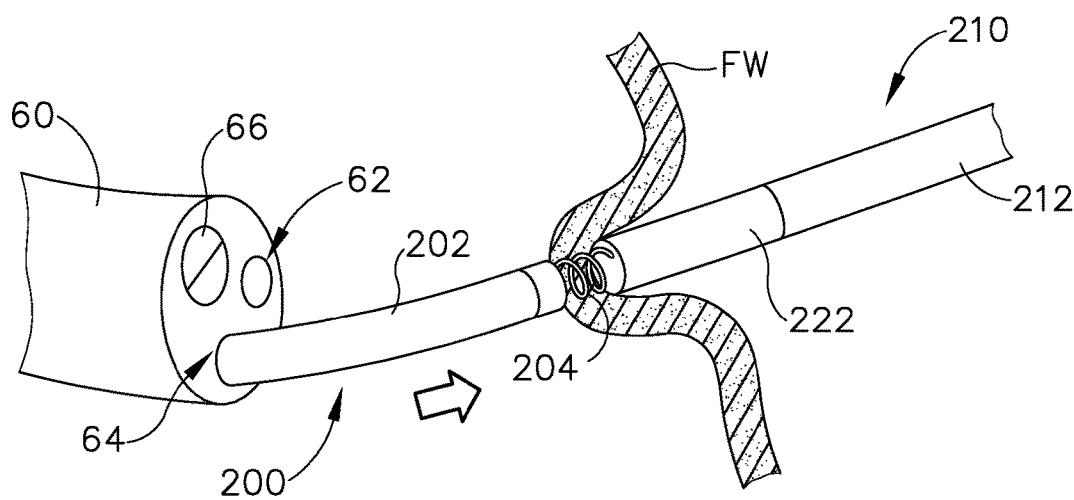
FIG. 11B depicts a schematic view of the end-grasp instrument of FIG. 11A deploying a helical anchor into the fundus wall to thereby grasp the fundus wall.

With distal tip (220) of balloon deployment instrument (210) bearing inwardly on the exterior of the fundus wall (FW), end-grasp instrument (200) is advanced toward the opposing side of the fundus wall (FW) and is actuated to deploy helical engagement feature (204) in the fundus wall (FW) as shown in FIG. 11B. By way of example only, shaft (202) may be rotated to drive helical engagement feature (204) like a corkscrew into the fundus wall (FW). Helical engagement feature (204) is sized and configured such that helical engagement feature (204) may be substantially embedded in the fundus wall (FW) without passing completely through the fundus wall (FW). Thus, helical engagement feature (204) does not contact distal tip (220) or balloon (200) of balloon deployment instrument (210), despite helical engagement feature (204) being positioned at the same region of the fundus wall (FW) as distal tip (220). With helical engagement feature (204) embedded in the fundus wall (FW), end-grasp instrument (200) may stabilize the fundus wall (FW) for the subsequent steps described below.

Figure 11C:
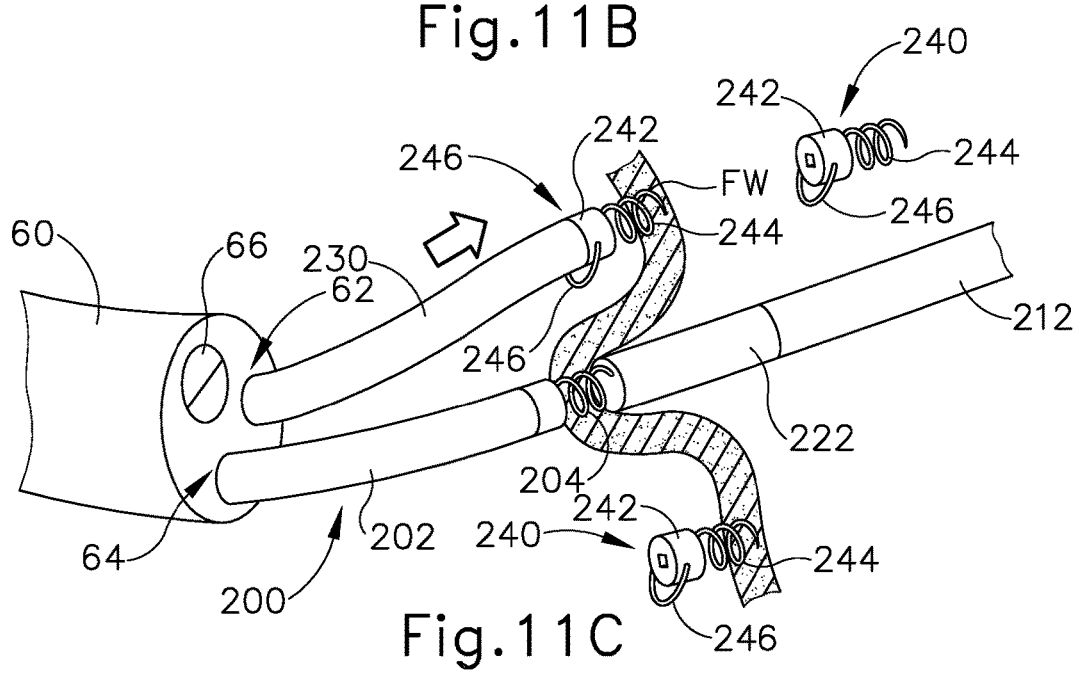
FIG. 11C depicts a schematic view of an anchor applier instrument deploying tissue anchors at several locations in the fundus wall near the location where the balloon deployment instrument is pushing against the exterior side of the fundus wall.

While balloon deployment instrument (210) and end-grasp instrument (200) remain stationary, an anchor applier instrument (230) is advanced via working channel (62) of gastroscope (60) to deploy a plurality of tissue anchors (240) in the fundus wall (FW), as shown in FIG. 11C. In the present example, each tissue anchor (240) includes a head (242) with a helical engagement feature (244) and a loop member (246). Anchor applier instrument (230) may drive tissue anchors (240) into the fundus wall (FW) by rotating tissue anchors (240), thereby driving helical engagement features (244) in a corkscrew fashion into the tissue of the fundus wall (FW). Alternatively, tissue anchors (240) may take a variety of other forms and may be secured to the tissue of the fundus wall (FW) in various other ways. Tissue anchors (240) are positioned in an arrangement surrounding the deformation of the fundus wall (FW) that is caused by the inwardly urged balloon deployment instrument (210). While three tissue anchors (240) are shown as being deployed, any other suitable number of tissue anchors (240) may be deployed. After tissue anchors (240) are deployed, anchor applier instrument (230) may be withdrawn from working channel (62).

Figure 11D:
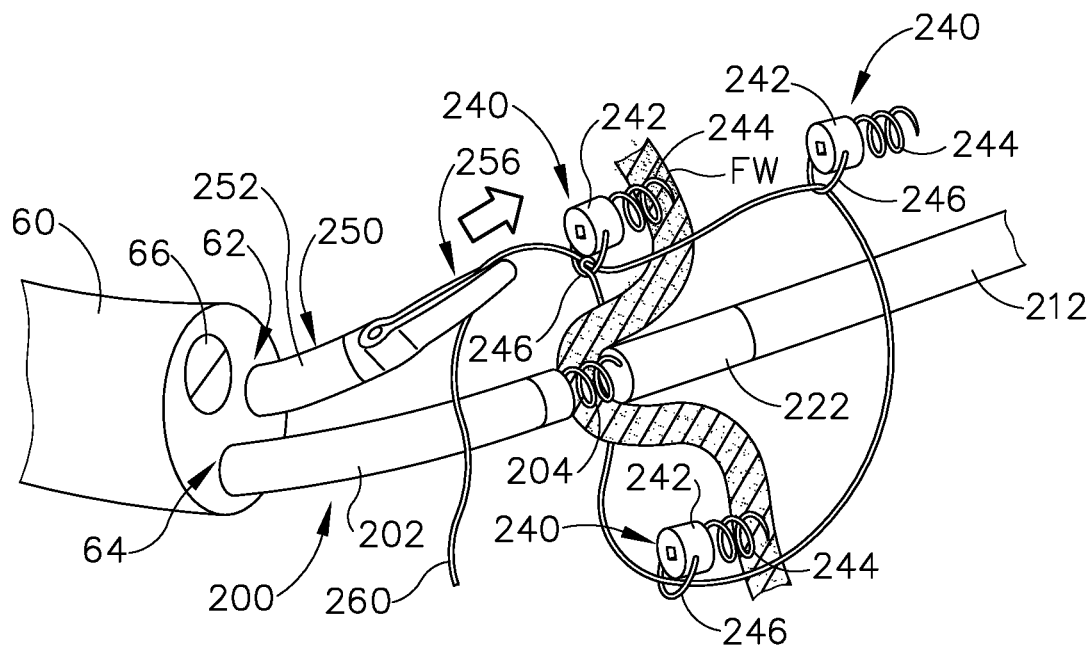
FIG. 11D depicts a schematic view of an exemplary grasping instrument securing a suture around the tissue anchors of FIG. 11C.
Figure 11E:
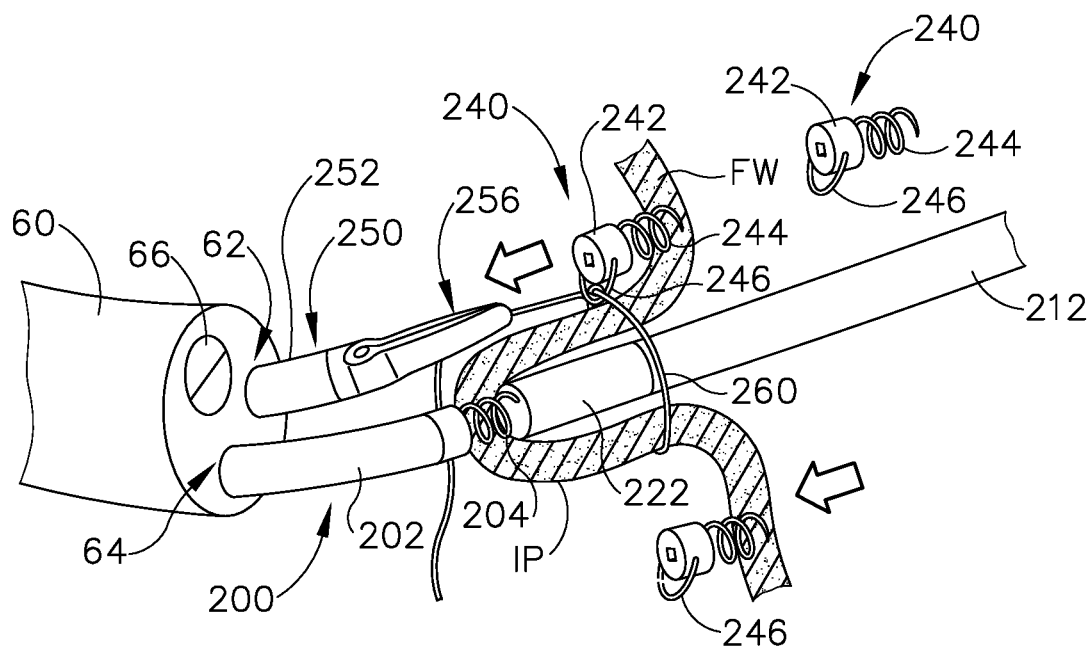
FIG. 11E depicts a schematic view of the balloon deployment instrument of FIG. 11 pushing further into the fundus wall to provide a more pronounced inverted portion of the fundus wall, with the grasping instrument of FIG. 11D pulling the suture to cinch the suture around a base region of the inverted portion of the fundus wall.

A grasping instrument (250) may then be introduced through working channel (62). Grasping instrument (250) of this example includes a shaft (252) and a pair of grasping jaws (256). Jaws (256) grasp a suture (260) in this example, and grasping instrument (250) is used to position suture through loop members (246) of tissue anchors (240) as shown in FIG. 11D. Suture (260) thus surrounds the deformation of the fundus wall (FW) that is caused by the inwardly urged balloon deployment instrument (210). Balloon deployment instrument (210) is then urged further inwardly into the fundus wall (FW), thereby enlarging an inverted portion (IP) of the fundus wall (FW) by increasing the plication depth as shown in FIG. 11E. As balloon deployment instrument (210) is then urged further inwardly into the fundus wall (FW), end-grasp instrument (200) is retracted proximally through a similar range of motion. Grasping instrument (250) is then used to pull suture (260) to thereby partially cinch suture (260) around the base of the inverted portion (IP), as is also shown in FIG. 11E.

As grasping instrument (250) pulls suture (260) to partially cinch suture (260) around the base of the inverted portion (IP), loop members (246) release suture (260). By way of example only, loop members (246) may include a pair of resilient wire segments that are configured to retain suture (260) until a sufficient force is used to pull suture (260) against the wire segments, at which point the wire segments separate enough to allow suture (260) to be pulled free. Other suitable ways in which loop members (246) may selectively retain and release suture (260) will be apparent to those skilled in the art in view of the teachings herein.

Figure 11F:
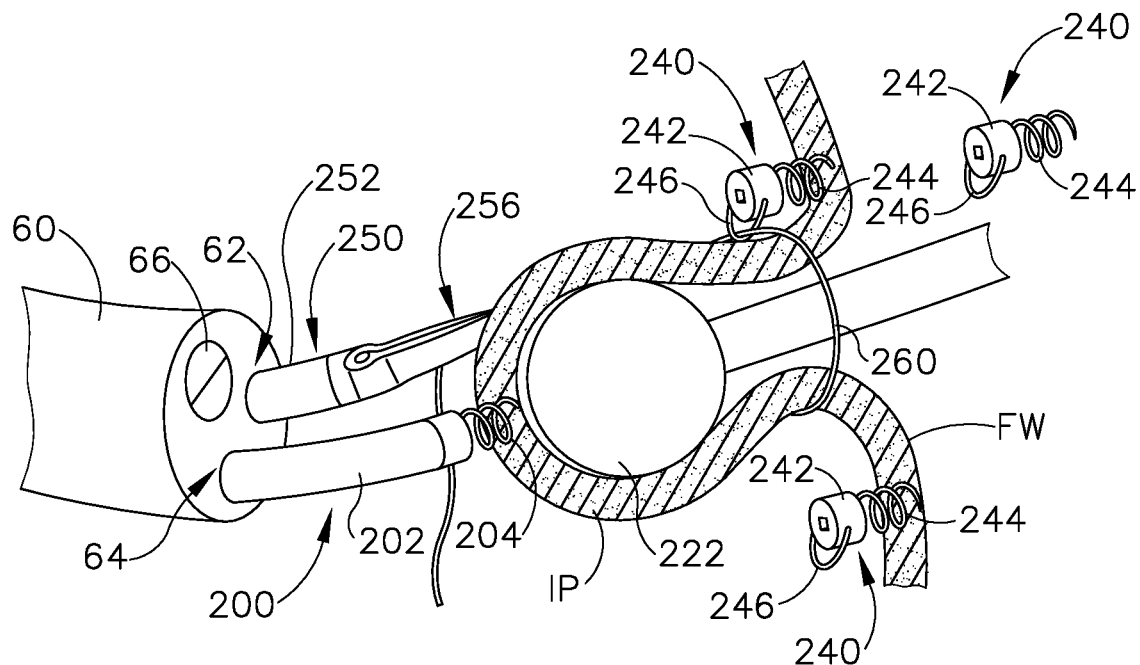
FIG. 11F depicts a schematic view of a balloon of the balloon deployment instrument of FIG. 11 inflated to enlarge the inverted portion of the fundus wall.
Figure 11G:
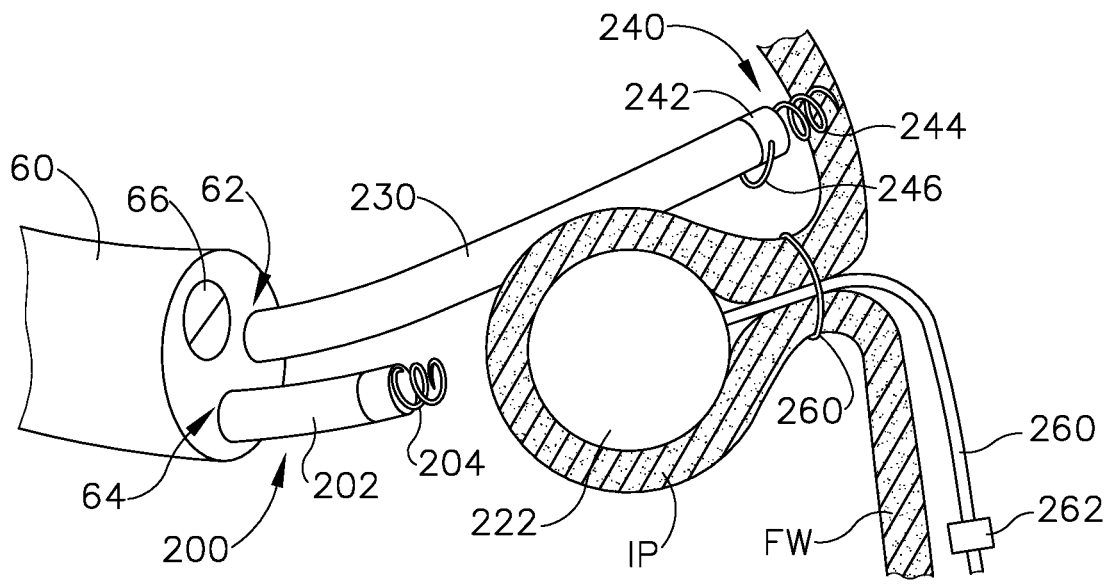
FIG. 11G depicts a schematic view of the end-grasp instrument of FIG. 11A removed from the fundus wall, with the anchor applier instrument of FIG. 11C removing the tissue anchors from the fundus wall, with the suture fully cinched around the base region of the enlarged inverted portion of the fundus wall, and with a shaft of the balloon deployment instrument of FIG. 11 removed to leave behind a tube and clip secured to the inflated balloon.

With suture (260) partially cinched around the base of the inverted portion (IP), balloon (222) is then inflated to further enlarge the inverted portion (IP) as shown in FIG. 11F. As noted above with respect to balloon (22), balloon (222) may be inflated to achieve a predetermined outer diameter; and this may be accomplished through the configuration of a fluid source that is in communication with balloon (222). Grasping instrument (250) is then used to further pull suture (260) to thereby further cinch suture (260) around the base of the inverted portion (IP), as shown in FIG. 11G. As noted above with respect to cinch assembly (30), suture (260) may be manipulated to define a predetermined inner diameter. By way of example only, this prescribed inner diameter may be achieved by providing visual, audible, or tangible feedback signaling that the target diameter has been achieved (e.g., instrument readout, camera, audible click, etc.). As also shown in FIG. 11G, anchor applier instrument (230) is used to remove tissue anchors (240) from the fundus wall (FW). End-grasp instrument (200) is disengaged from the fundus wall (FW) and is retracted through working channel (64); and shaft (212) is removed from balloon (222). The inflated balloon (220) is captured in the inverted portion (IP) of the fundus wall (FW) and is retained therein by cinched suture (260). The presence of inverted portion (IP) reduces the effective volume of the stomach (S). As noted above, this reduction of stomach (S) volume may result in weight loss for the patient, through an accelerated gastric emptying rate or other mechanism. As also described above, this reduction of stomach (S) volume may be provided on a temporary or permanent basis.

As is also shown in FIG. 11G, a tube (260) and a clip (262) extend from balloon (260) and are positioned at the exterior of the stomach (S). This configuration may allow a physician to later adjust the inflation of balloon (260)—either adding more fluid to further enlarge the inverted portion (IP) or removing fluid to deflate balloon (260). In other variations, clip (262) may be replaced with a valve or other feature. Alternatively, tube (260) and clip (262) may be omitted altogether. As yet another merely illustrative variation, balloons (22, 120) may include features like tube (260) and clip (262), if desired.

E. Exemplary Alternative Expandable Assembly

Figure 12:
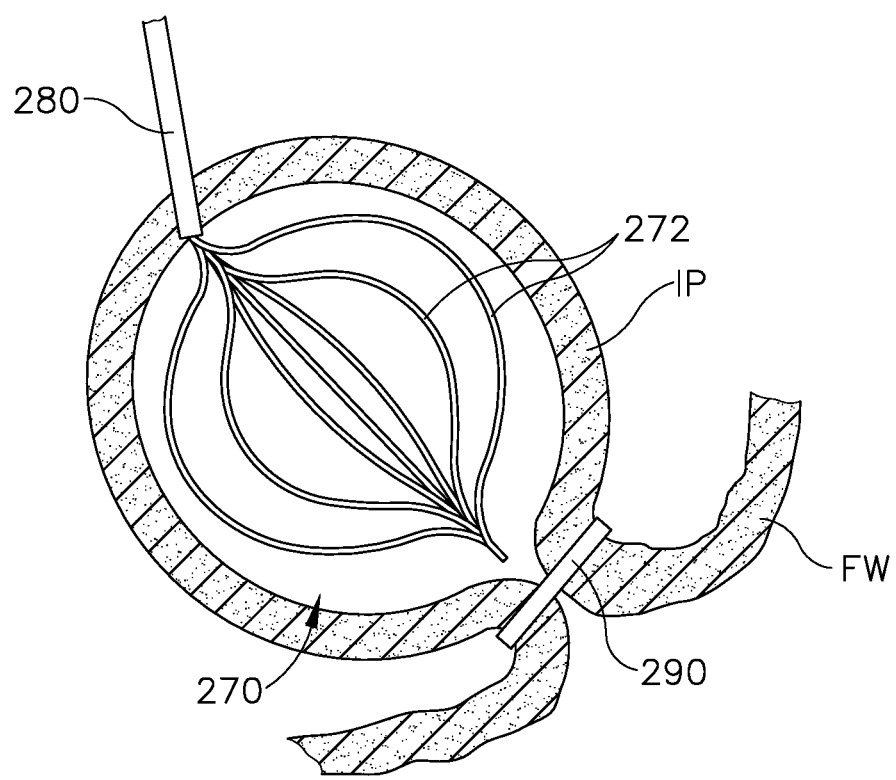
FIG. 12 depicts a perspective view of an exemplary alternative expandable assembly that may be used as a substitute for a balloon.

While the foregoing examples use balloons (22, 120, 222) to enlarge an inverted portion (IP) of a fundus wall (FW), and to maintain the enlargement, various other suitable structures may be used to perform the same task. By way of example only, FIG. 12 shows an exemplary alternative expandable assembly (270) at the distal end of a deployment shaft (280). Expandable assembly (270) includes a plurality of beams (272) that are joined together at their proximal and distal ends. Beams (272) are resiliently biased to provide the expanded configuration shown in FIG. 12, where beams (272) bow outwardly and are angularly spaced from each other, thereby defining a bulbous shape. A sheath (not shown) may be used to constrain beams (272) until beams (272) are suitably positioned through the fundus wall (FW), and then the sheath may be retracted to allow beams (272) to resiliently bow outwardly to create and maintain an expanded inverted portion (IP) of the fundus wall (FW). Beams (272) may thus have sufficient resiliency to expand an inverted portion (IP) of the fundus wall (FW). The constrained expandable assembly (270) and shaft (280) may be introduced via a gastroscope (60) as described above; or may otherwise be introduced. As noted above, the procedure associated with what is depicted in FIG. 12 may be performed at other regions of the stomach (S) and is not necessarily limited to the fundus wall (FW). The reference to the fundus wall (FW) in this merely illustrative example should not be viewed as limiting in any way.

A cinching assembly (290), which may be configured and operable in accordance with any of the teachings herein, may be secured to the base of the inverted portion (IP) to thereby capture expandable assembly (270) in the inverted portion (IP). Shaft (280) may be broken away from expandable assembly (270) and removed from the stomach (S), thereby leaving the expanded expandable assembly (270) in the inverted portion (IP). The presence of inverted portion (IP) reduces the effective volume of the stomach (S). As noted above, this reduction of stomach (S) volume may provide an accelerated gastric emptying rate, which may in turn result in weight loss for the patient.

Expandable assembly (270) may include various other structural elements in addition to or in lieu of including beams (272). By way of example only, expandable assembly (270) may include a mesh or cage that is resiliently biased to assume an expanded configuration. Other suitable forms that a non-inflatable expandable assembly (270) may take will be apparent to those of ordinary skill in the art in view of the teachings herein. As another merely illustrative example, an expandable assembly may include malleable members positioned about an inflatable balloon, such that the balloon is operable to transition the malleable members to form an expanded configuration; and the malleable members are able to maintain the expanded configuration even after the balloon is deflated or removed.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of reducing a volume of a stomach of a patient, the method comprising: (a) inverting a portion of a stomach wall to thereby create an inverted portion, wherein the stomach wall has an inner surface and an outer surface; (b) positioning an expandable member adjacent to the outer surface of the inverted portion; (c) expanding the expandable member to thereby expand the inverted portion, wherein the expanded expandable member has a first outer diameter; and (d) expanding the expandable member to thereby expand the inverted portion, wherein the expanded expandable member has a first outer diameter; wherein expanding and cinching provide a cinch diameter to first outer diameter ratio from approximately 0.5:1 to approximately 0.9:1.

Example 2

The method of Example 1, wherein cinching the base region comprises cinching a cinch assembly around an inner surface of the stomach wall at the base region of the inverted portion.

Example 3

The method of Example 2, wherein the cinch assembly comprises a strap and a head, wherein the head comprises a driving element configured to drive the strap through the head, wherein cinching the cinch assembly comprises driving the driving element.

Example 4

The method of Example 3, wherein the strap includes teeth, wherein the head includes a gear in a meshing relationship with the teeth, wherein driving the driving element comprises rotating the gear to drive the strap via the teeth.

Example 5

The method of any one or more of Examples 2 through 4, further comprising urging the cinch assembly against the inner surface of the stomach wall before inverting the portion of the stomach wall.

Example 6

The method of Example 5, wherein the cinch assembly forms a loop, wherein the inverting a portion of the stomach wall comprises pulling the portion of the stomach wall through the loop.

Example 7

The method of Example 6, wherein inverting a portion of the stomach wall comprises: (i) passing an expandable member instrument through the loop and further the stomach wall, (ii) partially expanding the expandable member outside of the stomach wall, and (iii) pulling the expandable member instrument proximally to thereby pull the portion of the stomach wall through the loop.

Example 8

The method of Example 7, wherein the loop forms a second inner diameter before inverting the portion of the stomach wall, wherein partially expanding the expandable member outside of the stomach wall comprises expanding the expandable member to define the second outer diameter, wherein the second outer diameter is smaller than the first inner diameter.

Example 9

The method of Example 8, wherein expanding the expandable member to thereby expand the inverted portion comprises expanding the expandable member to define the first outer diameter, wherein the first outer diameter is larger than the second outer diameter.

Example 10

The method of Example 9, wherein cinching a base region of the inverted portion comprises actuating the cinch assembly such that the loop forms the cinch diameter, wherein the cinch diameter is smaller than the first inner diameter.

Example 11

The method of Example 10, wherein the first outer diameter is larger than the cinch diameter.

Example 12

The method of claim 1, wherein the expandable member comprises a balloon, wherein expanding the expandable member comprises inflating the balloon.

Example 13

The method of any one or more of Examples 1 through 12, further comprising: (a) advancing an expandable member instrument through an abdominal wall; and (b) engaging the outer surface of the stomach wall with a distal portion of the expandable member instrument; wherein inverting the portion of the stomach wall comprises pushing the expandable member instrument against the outer surface of the stomach wall.

Example 14

The method of Example 13, further comprising anchoring an end-grasping instrument against the stomach wall from the inside of the stomach at a location on the opposite side of the stomach wall of the distal portion of the expandable member instrument.

Example 15

The method of any one or more of Examples 1 through 14, further comprising: (a) deploying a plurality of tissue anchors around the inverted portion of the stomach wall, from an inside region of the stomach; and (b) removably securing a suture to the tissue anchors; wherein cinching the base region of the inverted portion comprises cinching the suture about the base region of the inverted portion.

Example 16

The method of any one or more of Examples 1 through 15, further comprising un-expanding the expandable member after one or more predetermined conditions occur.

Example 17

The method of any one or more of Examples 1 through 15, further comprising leaving the inverted portion in a cinched state until tissue adjacent to the inverted portion necroses.

Example 18

A method of reducing a volume of a stomach of a patient, the method comprising: (a) positioning an expandable member adjacent to an outer surface of a stomach wall; (b) partially expanding the expandable member to define a first outer diameter; (c) urging the expandable member toward an interior region of the stomach wall, thereby creating an inverted portion; (d) expanding the expandable member to define a second outer diameter, wherein the second outer diameter is larger than the first outer diameter, thereby expanding the inverted portion; and (e) cinching a base region of the inverted portion to thereby capture the expanded expandable member in the expanded inverted portion.

Example 19

The method of Example 18, wherein positioning the expandable member comprises passing the expandable member through the stomach wall, from an interior region of the stomach to an exterior region of the stomach.

Example 20

A method of reducing a volume of a stomach of a patient, the method comprising: (a) positioning an expandable member adjacent to an outer surface of a stomach wall, wherein positioning the expandable member comprises either: (i) passing the expandable member through the stomach wall, from an interior region of the stomach to an exterior region of the stomach, or (ii) passing the expandable member through an abdominal wall, from a region exterior to the patient to a region that is interior to the abdominal wall but exterior to the stomach; (c) urging the expandable member toward an interior region of the stomach wall, thereby creating an inverted portion; (d) expanding the expandable member, thereby expanding the inverted portion; and (e) cinching a base region of the inverted portion to thereby capture the expanded expandable member in the expanded inverted portion.

Example 21

A kit, comprising: (a) an expandable member, wherein the expandable member is configured to be transitioned between a non-expanded state and an expanded state, wherein the expandable member in the non-expanded state is sized to pass through a human esophagus, wherein the expandable member is configured to define a first outer diameter in the expanded state; and (b) a cinch assembly, wherein the cinch assembly is sized to pass through a human esophagus, wherein the cinch assembly is configured to apply a cinch diameter to a base region of a wall of a human stomach and thereby capture the expanded expandable member in an inverted portion of the stomach wall, wherein the expandable member and the cinch assembly are configured to provide a cinch diameter to first outer diameter ratio from approximately 0.5:1 to approximately 0.9:1.

Example 22

The kit of Example 21, wherein the expandable member comprises a balloon.

Example 23

The kit of any one or more of Examples 21 through 22, further comprising a shaft having a distal end, wherein the expandable member is positioned at the distal end of the shaft.

Example 24

The kit of Example 23, wherein the distal end of the shaft further includes a tissue piercing feature, wherein the expandable member is positioned proximal to the tissue piercing feature.

Example 25

The kit of any one or more of Examples 21 through 24, further comprising a shaft having a distal end, wherein the cinch assembly is positioned at the distal end of the shaft.

Example 26

The kit of any one or more of Examples 21 through 25, wherein the cinch assembly comprises a strap.

Example 27

The kit of Example 26, wherein the cinch assembly further comprises a head secured to a first end of the strap, wherein a second end of the strap is configured to pass through the head to form a loop.

Example 28

The kit of Example 27, wherein the head includes a locking feature configured to selectively secure the position of the second end of the strap relative to the head.

Example 29

The kit of any one or more of Examples 27 through 28, further comprising a shaft having a distal end, wherein the cinch assembly is positioned at the distal end of the shaft, wherein the shaft includes a winding feature configured to drive movement of the second end of the strap relative to the head.

Example 30

The kit of any one or more of Examples 21 through 25, wherein the cinch assembly comprises: (i) a plurality of beads, and (ii) a plurality of links slidably coupling the beads together.

Example 31

The kit of Example 30, wherein the beads are magnetically attracted to each other.

Example 32

The kit of any one or more of Examples 21 through 31, further comprising an end-grasp instrument having a distal end feature that is configured to grasp tissue.

Example 33

The kit of Example 32, wherein the distal end feature of the end-grasp instrument has a helical configuration.

Example 34

The kit of any one or more of Examples 21 through 33, further comprising a set of tissue anchors, wherein the cinch assembly is configured to temporarily engage the tissue anchors.

Example 35

The kit of any one or more of Examples 21 or 23 through 34, wherein the expandable member comprises a plurality of beams arranged in an angularly spaced array.

III. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein, is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. or by an endoluminal robotic system such as the MONARCH™ system by Auris Health, Inc. of Redwood City, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of reducing a volume of a stomach of a patient, the method comprising:
   (a) inverting a portion of a stomach wall to thereby create an inverted portion, wherein the stomach wall has an inner surface and an outer surface;
   (b) positioning an expandable member adjacent to the outer surface of the stomach wall;
   (c) inserting a distal end of an end-grasping instrument into an interior of the stomach;
   (d) anchoring the end-grasping instrument onto an opposite side of the stomach wall relative to the expandable member by extending at least one anchor applying instrument distally out of the distal end of the end-grasping instrument and into the stomach wall;
   (e) expanding the expandable member to thereby expand the inverted portion, wherein the expanded expandable member has a first outer diameter; and
   (f) cinching a base region of the inverted portion to thereby capture the expanded expandable member in the expanded inverted portion, wherein cinching comprises applying a cinch diameter to the base region;
   wherein expanding and cinching provide a cinch diameter to first outer diameter ratio from approximately 0.5:1 to approximately 0.9:1.

2. The method of claim 1, wherein cinching the base region comprises cinching a cinch assembly around the inner surface of the stomach wall at the base region of the inverted portion.

3. The method of claim 2, further comprising urging the cinch assembly against the inner surface of the stomach wall before inverting the portion of the stomach wall.

4. The method of claim 3, wherein the cinch assembly forms a loop, wherein the inverting a portion of the stomach wall comprises pulling the portion of the stomach wall through the loop.

5. The method of claim 4, wherein inverting a portion of the stomach wall comprises:
   (i) passing an expandable member instrument through the loop and further the stomach wall,
   (ii) partially expanding the expandable member outside of the stomach wall, and
   (iii) pulling the expandable member instrument proximally to thereby pull the portion of the stomach wall through the loop.

6. The method of claim 5, wherein the loop forms a first inner diameter before inverting the portion of the stomach wall, wherein partially expanding the expandable member outside of the stomach wall comprises expanding the expandable member to define a second outer diameter, wherein the second outer diameter is smaller than the first inner diameter.

7. The method of claim 6, wherein expanding the expandable member to thereby expand the inverted portion comprises expanding the expandable member to define the first outer diameter, wherein the first outer diameter is larger than the second outer diameter.

8. The method of claim 7, wherein cinching the base region of the inverted portion comprises actuating the cinch assembly such that the loop forms the cinch diameter, wherein the cinch diameter is smaller than the first outer diameter.

9. The method of claim 2, wherein the cinch assembly includes at least first, second, and third magnetic beads, the method further comprising magnetically attracting the first, second, and third beads to a radially contracted state.

10. The method of claim 1, wherein the expandable member comprises a balloon, wherein expanding the expandable member comprises inflating the balloon.

11. The method of claim 1, further comprising:
    (a) advancing an expandable member instrument through an abdominal wall; and
    (b) engaging the outer surface of the stomach wall with a distal portion of the expandable member instrument;
    wherein inverting the portion of the stomach wall comprises pushing the expandable member instrument against the outer surface of the stomach wall.

12. The method of claim 1, further comprising:
    (a) deploying a plurality of tissue anchors around the inverted portion of the stomach wall, from an inside region of the stomach; and
    (b) removably securing a suture to the tissue anchors;
    wherein cinching the base region of the inverted portion comprises cinching the suture about the base region of the inverted portion.

13. The method of claim 1, wherein anchoring the end-grasping instrument further comprises anchoring at least first and second tissue anchors of the end-grasping instrument into the stomach wall on an opposite side of the stomach wall to the expandable member.

14. A method of reducing a volume of a stomach of a patient, the method comprising:
    (a) introducing a cinch assembly in a linear configuration into the stomach of the patient;
    (b) inverting a portion of a stomach wall to thereby create an inverted portion, wherein the stomach wall has an inner surface and an outer surface;
    (c) positioning an expandable member adjacent to the outer surface of the stomach wall;
    (d) inserting a distal end of an end-grasping instrument into an interior of the stomach;
    (e) anchoring the end-grasping instrument onto an opposite side of the stomach wall relative to the expandable member by extending at least one anchor applying instrument distally out of the distal end of the end-grasping instrument and into the stomach wall;
    (f) expanding the expandable member to thereby expand the inverted portion, wherein the expanded expandable member has a first outer diameter;
    (g) forming the cinch assembly into a loop; and
    (h) cinching a base region of the inverted portion using the cinch assembly to thereby capture the expanded expandable member in the expanded inverted portion.

15. The method of claim 14, wherein cinching comprises applying a cinch diameter to the base region, wherein expanding and cinching provide a cinch diameter to first outer diameter ratio from approximately 0.5:1 to approximately 0.9:1.

16. The method of claim 14, wherein the cinch assembly includes at least first, second, and third magnetic beads, wherein cinching the base region of the inverted portion further comprises magnetically attracting the at least first, second, and third magnetic beads of the cinch assembly to radially contract and directly contact the inner surface of the stomach wall to thereby capture the expanded expandable member.

17. The method of claim 16, wherein capturing the expanded expandable member in the expanded inverted portion causes a first portion of the outer surface to contact a second portion of the outer surface.

18. A method of reducing a volume of a stomach of a patient, the method comprising:
(a) inverting a portion of a stomach wall to thereby create an inverted portion, wherein the stomach wall has an inner surface and an outer surface;
(b) positioning an expandable member adjacent to the outer surface of the stomach wall;
(c) expanding the expandable member to thereby expand the inverted portion, wherein the expanded expandable member has a first outer diameter; and
(d) magnetically attracting first, second, and third magnetic portions of a cinch assembly to directly contact the inner surface of the stomach wall and thereby capture the expanded expandable member in the expanded inverted portion so that a first portion of the outer surface contacts a second portion of the outer surface.

19. The method of claim 18, wherein the cinch assembly includes first, second, and third magnetic beads, wherein the first magnetic bead includes the first magnetic portion, the second magnetic bead includes the second magnetic portion, and the third magnetic bead includes the first magnetic portion, the method further comprising maintaining the cinch assembly in an annular arrangement so that the at least first and second magnetic beads slide along links to provide a variable effective diameter for the cinch assembly.

20. The method of claim 18, further comprising:
(a) inserting a distal end of an end-grasping instrument into an interior of the stomach; and
(b) anchoring the end-grasping instrument onto an opposite side of the stomach wall relative to the expandable member by extending at least one anchor applying instrument distally out of the distal end of the end-grasping instrument and into the stomach wall.

* * * * *